(12) United States Patent
Higashino et al.

(10) Patent No.: US 8,008,091 B2
(45) Date of Patent: Aug. 30, 2011

(54) MICRO ANALYSIS SYSTEM

(75) Inventors: Kusunoki Higashino, Osaka (JP);
Akihisa Nakajima, Sagamihara (JP);
Yasuhiro Sando, Amagasaki (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 1248 days.

(21) Appl. No.: 11/391,196

(22) Filed: Mar. 29, 2006

(65) Prior Publication Data
US 2006/0228812 A1 Oct. 12, 2006

(30) Foreign Application Priority Data

Apr. 1, 2005 (JP) .................................. 2005-106588
Apr. 6, 2005 (JP) .................................. 2005-109803

(51) Int. Cl.
*G01N 1/10* (2006.01)
(52) U.S. Cl. .............. 436/180; 422/63; 422/64; 422/65; 422/67; 422/500; 422/501
(58) Field of Classification Search .............. 422/63–67, 422/99–100, 500–501; 436/180
See application file for complete search history.

(56) References Cited

U.S. PATENT DOCUMENTS 6,391,623 B1 * 5/2002 Besemer et al. ........... 435/287.2
6,960,437 B2 * 11/2005 Enzelberger et al. ............. 435/6

FOREIGN PATENT DOCUMENTS

JP 2003-180350 7/2003

OTHER PUBLICATIONS

Japanese Patent Office, "Notice of Reasons for Refusal," Patent Application No. 2007-512524, mailed Jan. 25, 2011, (2 pgs.).
English translation of Japanese Patent Office, "Notice of Reasons for Refusal," Patent Application No. 2007-512524, mailed Jan. 25, 2011, (2 pgs.).

\* cited by examiner

*Primary Examiner* — Jyoti Nagpaul
(74) *Attorney, Agent, or Firm* — Finnegan, Henderson, Farabow, Garrett & Dunner, L.L.P.

(57) ABSTRACT

A micro integrated analysis system includes a testing chip, system main body and heat insulating section. The chip has a pump connecting section to communicate with micro pumps; a mixing flow path for mixing a specimen and reagent and for reaction processing by heating; and a testing flow path for performing a predetermined test of a mixed solution heated and processed for reaction. The system main body has a holding section to hold the testing chip; micro pumps for injecting a specimen and reagent; a heating section for heating the mixing flow path; and a detection section for performing a test in the testing flow path. The heat insulating section insulates flow path portions continuing from both an inlet end and outlet end of a heated flow path area of the mixing flow path, from heat of the heating section so as to prevent a rise in temperature.

14 Claims, 10 Drawing Sheets

MICRO ANALYSIS SYSTEM

This application is based on Japanese Patent Applications No. 2005-106588 filed on Apr. 1, 2005 and No. 2005-109803 filed on Apr. 6, 2005 in Japanese Patent Office, the entire content of which is hereby incorporated by reference.

FIELD OF THE INVENTION

The present invention relates to a testing micro chip that is applicable as a micro reactor to, for example, gene testing, and relates to a micro integrated analysis system and a testing method using the chip.

BACKGROUND OF THE INVENTION

In recent years, using micro-machine technology and microscopic processing technology, systems are developed in which devices and means, for example, pumps, valves, flow paths, sensors and the like for performing conventional sample preparation, chemical analysis, chemical synthesis and the like are miniaturized and integrated on a single chip.

These systems are called μ-TAS (Micro Total Analysis System), bioreactor, lab-on-chips, and biochips, and much is expected of their application in the fields of medical testing and diagnosis, environmental measurement and agricultural manufacturing.

As seen in genetic screening in particular, in the case where complicated steps, skilful operations, and machinery operations are necessary, a microanalysis system, which is automatic, has high speed and is simple, is very beneficial not only in terms of reduction in cost, required amount of sample and required time, but also in terms of the fact that it makes analysis possible in cases where time and place cannot be selected.

At a site where various testing such as clinical testing is carried out, even in a case of measuring with a microreactor of a chip type which can quickly output results regardless of place, quantitation and accuracy in analysis are deemed to be important.

In various analysis and tests, quantitation of analysis, precision of analysis and economy are major factors in the development of the aforementioned analysis chip capable of producing results independently of place. To achieve this purpose, it is important to establish a highly reliable liquid feed system of simple structure. Thus, there has been an active demand for a reliable, high-precision micro fluid control device. The present inventors have already proposed a micro pump system and a control method capable of meeting such requirements (Patent Documents 2 to 4).

In order to cause reaction between a specimen and reagent and transport a reaction product to a detection part by the use of such a micro pump and detect the reaction product such that the related operations can be performed in a single chip, a serial micro flow path is formed in the chip. In this case, it is necessary to integrate and dispose a flow path system including storage sections for a specimen and reagents, a mixing section to mix the reagents, a reaction section, a detection section, and flow paths to communicate these sections, and accompanying function elements, densely in a limited space.

Furthermore, the inventors of the present invention have already proposed, in Patent Document 5 (Japanese Patent Application TOKUGAN No. 2004-138959), a testing microchip (microreactor) including: a specimen storage section in which specimen is stored; a reagent storage in which reagent is stored; a reaction section which has a reaction flow path in which the specimen stored in the specimen storage section and the reagent stored in the reagent storage section are merged to perform a predetermined reaction processing; and a testing section which has a testing path for performing a predetermined test on the reaction-processed substance obtained from the reaction in the reaction section, wherein the specimen storage section, the reagent storage section, the reaction section, and the testing section are connected continuously by a serial flow path from the upstream side to the downstream side.

That is, a testing micro chip 100 of a prior art, as disclosed in Patent Document 5, includes a specimen storage section 104 for storing a specimen 102 and reagent storage sections 108 in which reagents 106 are sealed in advance.

The micro chip 100 also includes a mixing flow path 110 in which the reagents 106 stored in the reagent storage sections 108 are mixed. The mixed reagent mixed in the mixing flow path 110 and the specimen 102 from the specimen storage section 104 are mixed through a Y shape flow path or the like. A reaction flow path 112 is provided in which reaction is started by a heater 116 or the like.

Further, the specimen having been caused to react with the mixed reagent in the reaction flow path 112 is transported to the downstream side of the flow path 114 and the reaction is detected at a detection part that is provided on an analysis flow path 114.

With such a testing micro chip of a prior art, in a case, foe example, where a testing micro chip 100 performs an amplification reaction by ICAN method (Isothermal chimera primer initiated nucleic acid amplification), the specimen storage section 104 stores a specimen extracted from blood or sputum.

On the other hand, biotin-modified chimera-primer, DNA polymerase having a strand displacement activity and a reagent containing endonuclease hybridize are stored in the reagent storage sections 108, to specifically hybridize with a gene being a detection object.

Accordingly, when the mixed reagent having been mixed in the mixing flow path 110 and the specimen 102 from the specimen storage section 104 are mixed through a Y shape flow path or the like and mixed in the reaction flow path 102, gene amplification reaction is promoted in such a manner that a heater 116 which is, for example, a nichrome wire heater, sheathed heater, heater formed with an ITO membrane or a metallic membrane (chrome, gold, platinum, etc.) on a substrate is applied under heat control to the range 50 to 65° C., for example, to 55° C.

With an example of an amplification reaction by a PCR (polymerase chain reaction) method, it is necessary to heat a flow path that constructs the reaction part and also, if necessary, a flow path which performs preprocessing, to a predetermined temperature. On the other hand, there are also regions which are desirably not to rise in temperature, in the serial micro flow path including a number of function parts. For example, many of specimens and reagents tend to denature when heated and need cooling to avoid it. Parts where such specimens or reagents are stored or parts where reagents are mixed with each other require selective heat dissipation or cooling.

In a chip that contains an integrated serial micro flow path in a limited space, in a case where a flow path which is adjacent to a reaction part to be heated and for which a rise in temperature is undesirable is disposed, or in a case where non-satisfactory temperature distribution may cause a problem on reaction, it is necessary to prevent transfer of heat from the heated part to flow paths near the section. For example, when a part of a liquid in a flow path is heated and if meniscus (the front end boundary surface of a liquid in a flow path) of a liquid is present in a heated area, to be heated, or its vicinity, liquid may evaporate from the meniscus. This may affect the accuracy of quantitation and cause various problems. Especially, in a case where liquid is fed to a successive reaction process section after a heating process of the liquid in a µTAS is completed at a heating section, it is necessary to keep the liquid at the place where it is in the heated area for a certain time, which tends to cause the above described problems.

| | |
|---|---|
| [Patent Document 1] | TOKKAI No. 2004-28589 |
| [Patent Document 2] | TOKKAI No. 2001-322099 |
| [Patent Document 3] | TOKKAI No. 2004-108285 |
| [Patent Document 4] | TOKKAI No. 2004-270537 |
| [Patent Document 5] | TOKUGAN No. 2004-138959 |

[Non-patent Document] "DNA Chippu-gijutu To Sono Ouyou (DNA chip technology and application)" and No. 13 of Volume 43 of "Tanpakushitu Kakusan Kouso (Protein, Nucleic acid and Enzyme)" (1998) written by Fusao Kimizuka and Ikunoshin Kato and published by Kyoritsu Shuppan Co., LTD.

However, heating with these kinds of heaters may cause gas bubbles in the mixed liquid between a specimen and reagent if the heating time by the heater is long. The gas bubbles function to inhibit coupling between biotin-modified chimera-primer that specifically hybridizes with a gene being a detection object and a specimen, which may prohibits a predetermined test in a testing section.

Further, long time heating with these kinds of heaters causes a side-reaction other than reaction between a specimen and reagent. That is, a side-reaction by various materials other than a target material occurs, and amplified products of which inhibit amplification of the target material. Consequently, analysis based on reaction as a predetermined purpose becomes difficult and a predetermined test in a testing section may not be achieved.

Still further with these kinds of heaters, even if heating is stopped, a certain time is required before a heater is cooled down. With such a residual heat time, gas bubbles and side reaction, as described above, may be caused by the inertia temperature.

Yet further, since the reagent 106 stored in the reagent storage section 108 has a characteristic of denaturing due to effect by temperature, such a long heating time and residual heat time may denature the reagent 106 stored in the reagent storage section 108, making it impossible to carry out a predetermined test in the testing section.

The present invention wad devised, taking problems into account, such as described above. An object of the invention is to provide a micro integrated analysis system and a method by the system which inhibit transfer of residual heat from a heating part to neighboring flow paths in a testing chip as much as possible, and includes a flow path structure that makes the temperature distribution in the chip to be rigorous as much as possible.

Further, another object of the invention is to provide a testing micro chip and a micro integrated analysis system using the chip, which are reliable. In this micro chip, when a mixed reagent having been mixed in a mixing path and a specimen from a specimen storage section meet with each other and get mixed in a mixing and reaction flow path, it is possible to quickly heat the mixture to a necessary temperature, to heat the mixture for a necessary time required for reaction when the temperature has reached the necessary temperature, and to quickly cool the mixture so that no gas bubbles are generated and no side reaction is caused. Thus, an accurate and correct test can be achieved.

SUMMARY OF THE INVENTION

In an aspect of the invention, there is provided a micro integrated analysis system, including:
a testing chip that includes:
    a pump connecting section having flow path openings to communicate with respective micro pumps;
    a mixing flow path for mixing a specimen and reagent injected by the respective micro pumps and for reaction processing by heating; and
    a testing flow path for performing a predetermined test of a mixed solution having been mixed and processed for reaction in the mixing flow path;
a system main body that includes:
    a holding section to hold the testing chip;
    micro pumps for injecting a specimen and reagent;
    a heating section for heating the mixing flow path of the held testing chip; and
    a detection section for performing a test of the mixed solution in the testing flow path of the testing chip; and
a heat insulating section provided in at least one of the testing chip and the system main body, insulating flow path portions continuing from an inlet end and outlet end of a heated flow path portion, to be heated, of the mixing flow path, from heat of the heating section.

In another aspect of the invention, in the micro integrated analysis system in the above aspect,
the heating section performs reaction processing of the mixed solution having been mixed, by heating the inlet end of the heated flow path immediately after the specimen and reagent are mixed in the mixing flow path; and
the heat insulating section cools the outlet end immediately after the reaction processing.

DETAIL DESCRIPTION OF THE PREFERRED EMBODIMENTS

Figure 1:
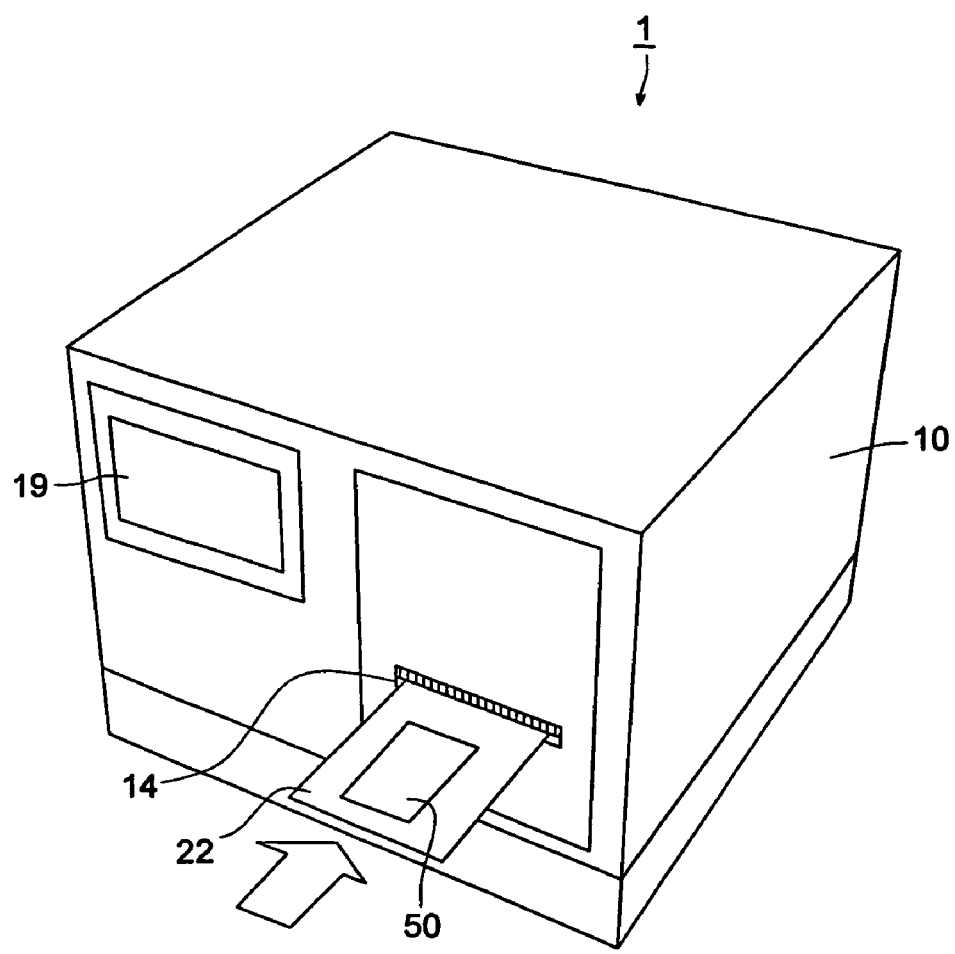
FIG. 1 is a schematic perspective view showing an embodiment of a micro integrated analysis system in accordance with the present invention.

The present invention includes the following structures and methods.

(Structure 1)

A micro integrated analysis system, including:
a testing chip that includes:
  a pump connecting section provided with flow path openings to communicate with micro pumps;
  a micro flow path;
  a heat insulating section that is included in a temperature adjusting area for the micro flow path and insulates both end portions of a micro flow path area, to be selectively heated, from heat from a heating side; and
a system main body that includes, at least:
  a base main body;
  a chip connecting section inside the base main body, having flow path openings to communicate with the testing chip;
  a micro pump unit that includes a plurality of micro pumps;
  a detection processing device; and
  a control device that controls, at least, a function of the micro pump unit and a function of the detection processing device,
wherein,
the testing chip gets mounted inside the base main body in a state where the pump connecting section of the testing chip and the chip connecting section of the micro pump unit are in a liquid tight contact with each other, and then the system analyzes a target material in a specimen in the testing chip.

(Structure 2)

The micro integrated analysis system of Structure 1, wherein the heat insulating section that insulates the both end portions of the micro flow path area, to be selectively heated, from heat from the heating side is a member that is in contact with the both end portions and cool the end portions.

(Structure 3)

The micro integrated analysis system of Structure 1, wherein the heat insulating section that insulates the both end portions of the micro flow path area, to be selectively heated, from heat from the heating side is heat insulating oil charged in the flow path at the both end portions.

(Structure 4)

The micro integrated analysis system of Structure 1, wherein the heat insulating section that insulates the both end portions of the micro flow path area, to be selectively heated, from heat from the heating side is micro flow paths of which cross sections are narrowed from that of the flow path at the both end portions and narrower than cross sections of flow paths before and after.

(Structure 5)

The micro integrated analysis system of any one of Structures 1 to 4, wherein the heat insulating section that insulates the both end portions of the micro flow path area, to be selectively heated, from heat from the heating side is made of a material with a thermal conductivity not greater than 10 W/m·K, at least, at said portions.

(Structure 6)

The micro integrated analysis system of any one of Structures 1 to 5, wherein the testing chip is formed with a serial micro flow path for feeding, after the testing chip is mounted in the base main body in a state where the pump connecting section of the testing chip and a chip connecting section of the micro pump unit are in tight liquid contact with each other, a specimen stored in a specimen storage section or a target material contained in a processing solution having been produced by processing the specimen in a flow path and feeding reagent stored in a reagent storage section to a flow path that includes a reaction part to cause mixing and reaction between the specimen or the target material and the reagent, and thereafter feeding a produced material by the reaction or a further processed material of it to a flow path for a detection part to measure the produced material or the further processed material with the detection processing device.

(Structure 7)

The micro integrated analysis system of any one of Structures 1 to 6, wherein the micro flow path that is included in the temperature adjusting area of the micro flow path and selectively heated is a flow path that forms a reaction part to cause reaction between the target material and reagent.

(Structure 8)

The micro integrated analysis system of Structure 6 or 7, wherein the system performs gene amplification reaction in a flow path that forms the reaction part.

(Structure 9)

The micro integrated analysis system of Structure 1, wherein the micro pump includes:
  a first flow path, disposed on the micro flow path, of which flow path resistance varies with a differential pressure;
  a second flow path, disposed on the micro flow path, of which variation rate of a flow path resistance to variation in a differential pressure is smaller than that of the first flow path;
  a pressing chamber that is disposed on the micro flow path and connected with the first flow path and the second flow path;
  an actuator that changes an inner pressure of the pressing chamber; and
  a driving device that drives the actuator.

(Structure 10)

A testing apparatus that uses a testing micro chip, the chip including:
  a specimen storage section that stores a specimen;
  a reagent storage section that stores reagent;
  a reaction section that has a reaction flow path to cause the specimen stored in the specimen storage section and the reagent stored in the reagent storage section to mix with each other and perform a predetermined reaction processing; and
  a testing section that has a testing flow path to perform a predetermined test of a reaction-processed material produced by reaction in the reaction section,
  wherein, the specimen storage section, the reagent storage section, the reaction section and the testing section are continuously connected through a serial flow path from an upstream-side to a downstream-side, and the apparatus includes a heating-cooling device that heats a mixed solution of the specimen and reagent immediately after the specimen stored in the specimen storage section and the reagent stored in the reagent storage section are mixed with each other in the reaction section, and performs reaction processing, and performs cooling immediately thereafter.

(Structure 11)

The testing apparatus of Structure 11, wherein the heating-cooling device is controlled such as to perform cooling during a time after heating the mixed solution of the specimen and reagent for reaction processing and before a cause of side reaction.

(Structure 12)

The testing apparatus of Structure 10 or 11, wherein the heating-cooling device is constructed with a Peltier element that performs heating-cooling by switching an electric current.

(Structure 13)

The testing apparatus of any one of Structures 10 to 12, wherein the heating-cooling device is structured with a heating unit and a cooling unit.

(Structure 14)

The testing apparatus of any one of 10 to 13, wherein the mixed solution of the specimen and reagent is cooled until just before the solution is heated and processed for reaction.

(Structure 15)

A testing microchip, including:
a specimen storage section that stores a specimen;
a reagent storage section that stores reagent;
a reaction section that has a reaction flow path to cause the specimen stored in the specimen storage section and the reagent stored in the reagent storage section to meet with each other and perform a predetermined reaction processing; and
a testing section that has a testing flow path to perform a predetermined test of a reaction-processed material produced by reaction in the reaction section,
wherein the specimen storage section, the reagent storage section, the reaction section and the testing section are continuously connected through a serial flow path from an upstream-side to a downstream-side, and
wherein the microchip includes a heating-cooling device that heats a mixed solution of the specimen and reagent immediately after the specimen stored in the specimen storage section and the reagent stored in the reagent storage section meet with each other in the reaction section and performs reaction processing, and performs cooling immediately thereafter.

(Structure 16)

The testing microchip of Structure 15, wherein the heating-cooling device is controlled such as to perform cooling during a time after heating the mixed solution of the specimen and reagent and performing reaction processing and before side reaction being caused.

(Structure 17)

The testing microchip of Structure 15 or 16, wherein the heating-cooling device is constructed with a Peltier element that performs heating and cooling by switching an electric current.

(Structure 18)

The testing microchip of any one of Structures 15 to 17, wherein the heating-cooling device is structured with a heating unit and a cooling unit.

(Structure 19)

The testing microchip of any one of Structures 15 to 18, wherein the mixed solution of the specimen and reagent is cooled until just before the solution is heated and processed for reaction.

(Structure 20)

A testing apparatus, wherein the apparatus is arranged such that the testing microchip of any one of Structures 15 to 19 is attachably and detachably mounted on the testing apparatus and the apparatus performs a test in the testing section of the testing microchip.

(Method 1)

A method for insulating both end portions of a micro flow path area that is selectively heated, the area being a part of a micro flow path provided in a testing chip for analysis of a target material in a specimen, the method employing at least one of:
forming at least the both end portions of the chip, using a material having a thermal conductivity not greater than 10 W/m·K;
having the both end portions in contact with a cooling member to cool the portions;
charging heat-insulating oil in the flow path at the both end portions; or
having a cross-sectional area of the micro flow path narrower at the both end portions than at portions before and after.

(Method 2)

A testing method that uses a testing micro chip, the chip including:
a specimen storage section that stores a specimen;
a reagent storage section that stores reagent;
a reaction section that has a reaction flow path to cause the specimen stored in the specimen storage section and the reagent stored in the reagent storage section to meet with each other and perform a predetermined reaction processing; and
a testing section that has a testing flow path to perform a predetermined test on a reaction-processed material produced by reaction in the reaction section,
wherein, the specimen storage section, the reagent storage section, the reaction section and the testing section are continuously connected through a serial flow path from an upstream-side to a downstream-side; and
a mixed solution of the specimen and reagent is heated immediately after the specimen stored in the specimen storage section and the reagent stored in the reagent storage section meet with each other and is subjected to reaction processing, and cooling is performed immediately thereafter, in the reaction section.

(Method 3)

The testing method of Method 2, wherein cooling is performed during a time after heating is performed on the mixed solution of the specimen and reagent for reaction processing and before a cause of side reaction.

(Method 4)

The testing method of Method 2 or 3, wherein heating and cooling is performed by switching an electric current with a Peltier element.

(Method 5)

The method of any one of Methods 2 to 4, wherein heating and cooling is performed by heating with a heating unit and cooling with a cooling unit.

(Method 6)

The method of any one of Methods 2 to 5, wherein the mixed solution of the specimen and reagent is cooled until just before the solution is heated and processed for reaction.

An embodiment of the present invention will be described below.

In the present specification, "a flow path element" is a function component installed on a testing chip. On the other hand, "a micro flow path" is a micro flow path in a groove form that is formed on a testing chip (micro reactor chip) in accordance with the invention. A storage section for reagent or the like, a reaction part or detection part, which is formed in a reservoir shape with a large capacity and width may also be referred to as "a micro flow path". In most cases, fluid that flows in a micro flow path is liquid, and more concretely, various type of reagent, specimen solution, denaturation agent solution, cleaning liquid, driving liquid, etc. The word "gene" means a DNA o RNA having genetic information for a certain function. However, "gene" may also means DNA or RNA that is a mere chemical substance. A target material to be an object of analysis may also be referred to as "analyte".

(Micro Integrated Analysis System)

A micro integrated analysis system in the present embodiment of the invention includes:

a testing chip having a pump connecting section with flow path openings to communicate with micro pumps, a micro flow path, a heat insulating device to insulate the both end portions of a micro flow path area that is included in a temperature adjusting area of the micro flow path and selectively heated, from heat from the heating side; and a system main body having, at least, a base main body, a chip connecting section that is disposed in the base main body and has flow path openings to communicate with the testing chip, a micro pump unit including a plurality of micro pumps, a detection processing device, and a control device to control, at least, the function of the micro pump unit and the function of the detection processing device, wherein the testing chip is mounted on the base main body in a state where the pump connecting section of the testing chip and the chip connecting section of the micro pump unit are in liquid tight contact, and then a target material in a specimen is analyzed in the testing chip.

The present invention allows arbitrary modifications and changes without departing from the spirit of the invention in various embodiments, and such modifications and change are included in the invention. That is, the entire or a part of a micro integrated analysis system in accordance with the invention can be changed variously as long as the structure, arrangement, disposition, shape, dimension, material, method, etc. accord with the spirit of the invention.

An embodiment in accordance with the invention will be described in detail below, referring to the drawings.

Figure 2:
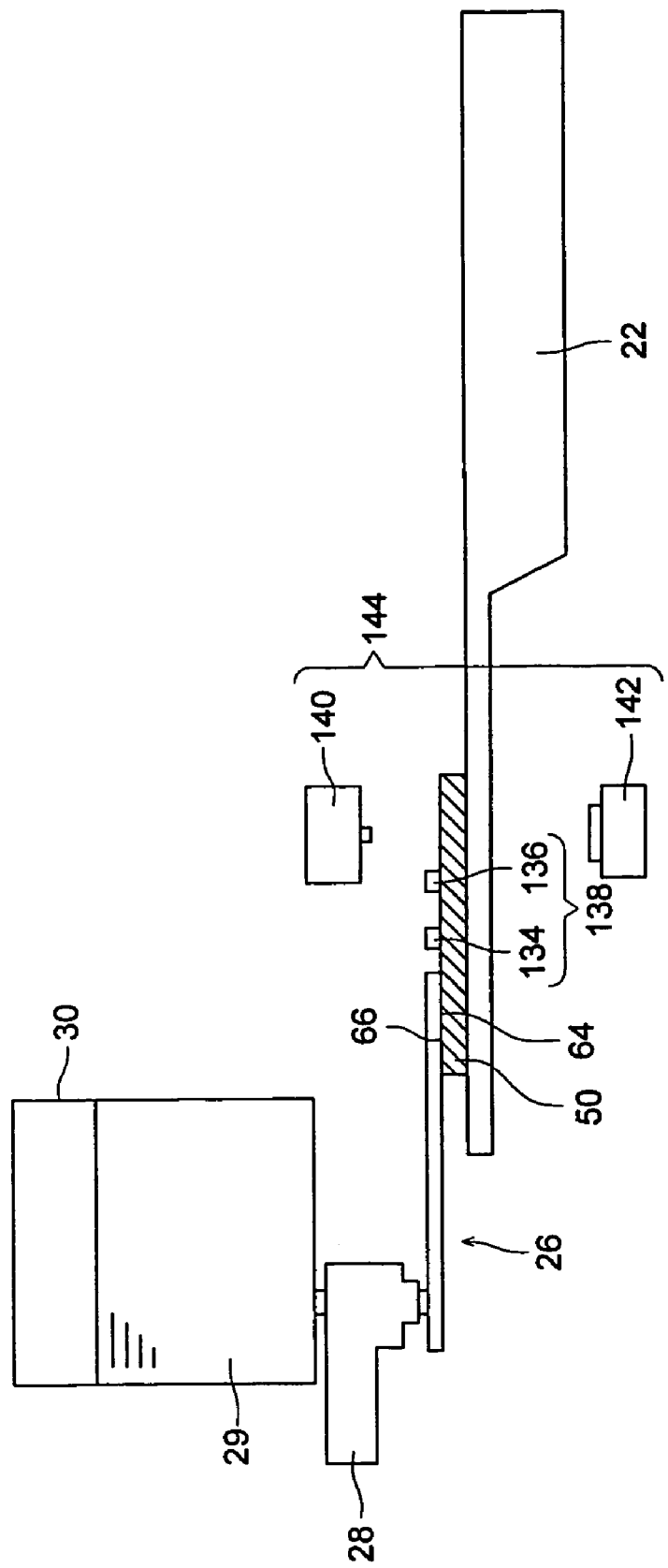
FIG. 2 is a schematic diagram of the inside of an apparatus main body of the micro integrated analysis system in FIG. 1, showing a state where a testing chip is mounted on a base main body.
Figure 10:
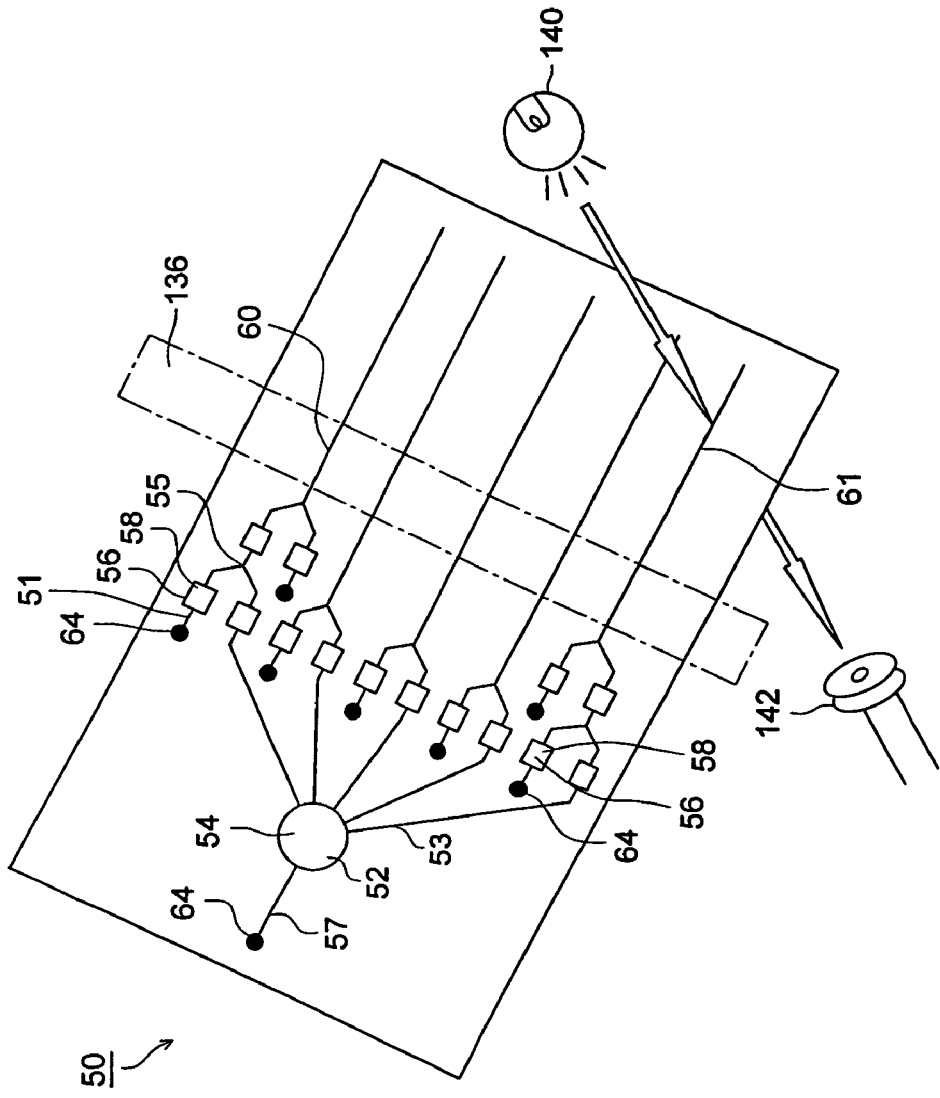
FIG. 10 is a schematic perspective view showing a testing microchip of the micro integrated analysis system in FIG. 1.
Figure 11:
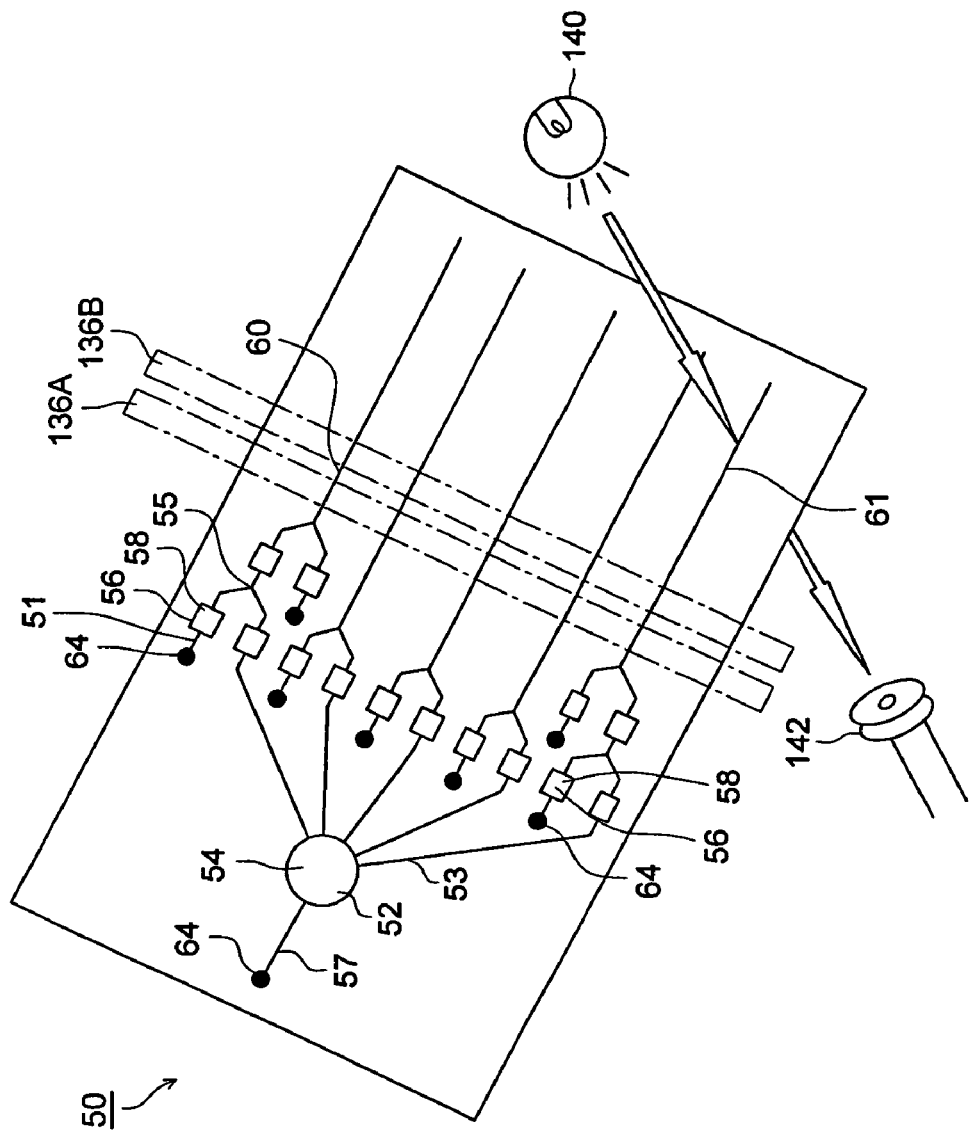
FIG. 11 is a schematic perspective view showing another example of a testing microchip of the micro integrated analysis system in FIG. 1.
Figure 12:
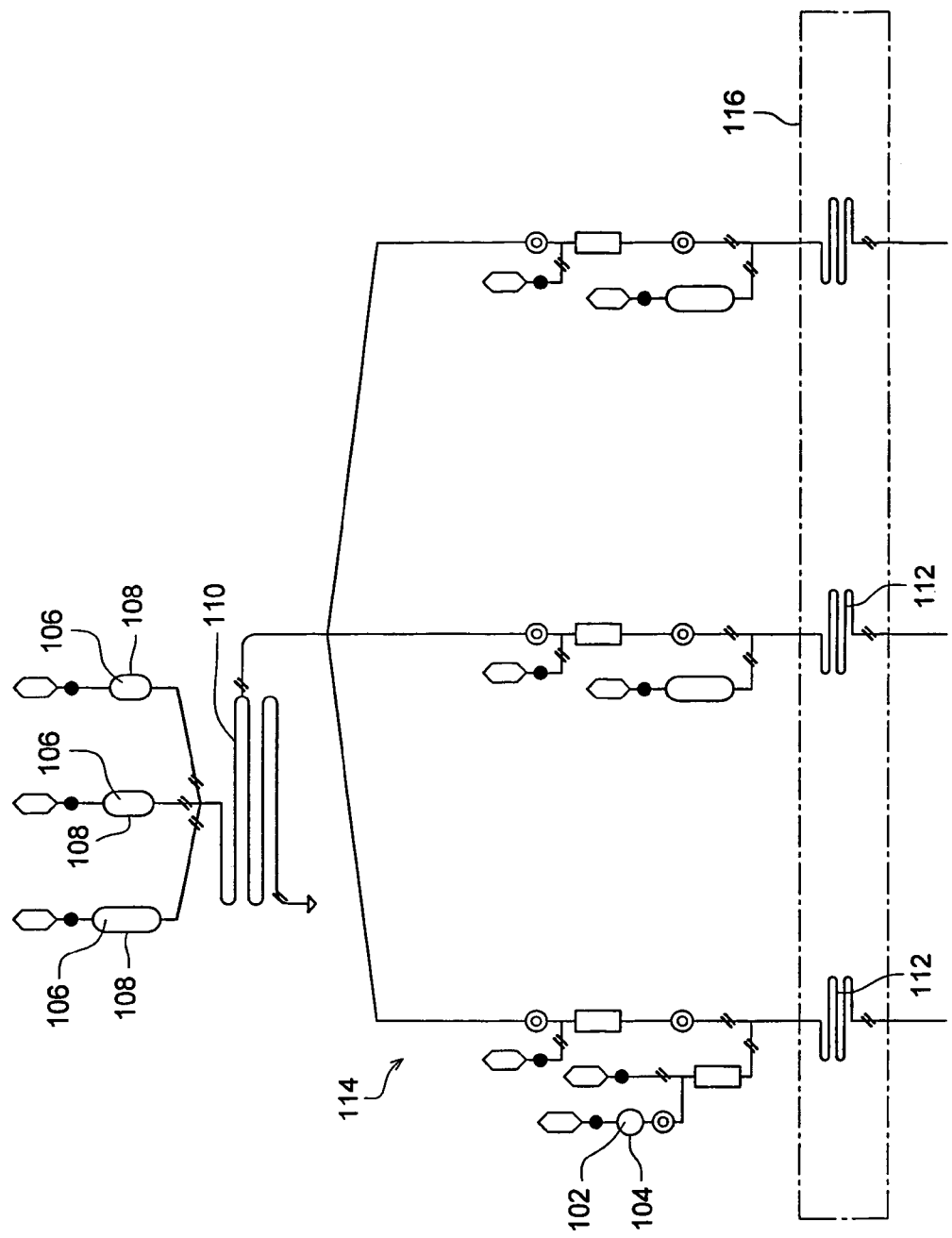
FIG. 12 is a schematic diagram of a testing microchip of a prior art.

FIG. 1 is a schematic perspective view showing an embodiment of a micro integrated analysis system in accordance with the present invention. FIG. 2 is a schematic diagram of the inside of an apparatus main body of the micro integrated analysis system in FIG. 1, showing a state where a testing chip is mounted on a base main body. FIG. 10 is a schematic perspective view showing a testing microchip of the micro integrated analysis system in FIG. 1.

In FIG. 1, reference numeral 10 denotes a micro integrated analysis system (hereinafter, also referred to merely as "analysis system") that uses a testing microchip in accordance with the invention.

The analysis system 1 is, as shown in FIG. 1, includes a system main body 10, and the system main body 10 is provided with a testing chip gateway 14 at the front thereof to take in a testing micro chip 50 and a display section 19 to output a test result of a predetermined test performed in the system main body 10.

The testing micro chip 50 is loaded on a chip conveying tray 22, and then taken into the system main body 10 via the testing chip gateway 14 to be mounted.

Inside the system main body 10, as shown in FIG. 2, various devices are provided to control liquid feed, reaction, detection, etc. in the testing microchip 50 loaded on the chip conveying tray 22.

In the present embodiment, there are provided a micro pump 26 that is connected with a pump connecting section 64 of the testing microchip 50 and transports a specimen and processing solution to predetermined places, and a pump control device 28 that performs liquid feed control of the micro pump unit 26.

FIG. 1 a conceptual diagram showing an embodiment of a micro integrated analysis system in accordance with the present invention. In the present embodiment, as shown, the system 1 includes the testing micro chip 50 and the system main body 10 as the apparatus to hold the chip. The system main body 10 includes a heating-cooling unit (Peltier element 134 and a heater 136) for reaction, a micro pump unit 26 having micro pumps for liquid feeding, a driving liquid tank 30 and a chip connecting section, a control device (not shown) related to various controls of liquid feeding, temperature, reaction and the like, and a detection processing device (not shown) that has an optical unit (an LED 140, a photo diode 142, etc.) and the like and also performs data collection (measurement) and processing.

Further, the testing microchip described above is attachably and detachably mounted on the micro integrated analysis system in the present embodiment in accordance with the invention, and the system performs test in a testing section of the testing microchip.

With such an arrangement, by just mounting a testing microchip that is convenient for carrying an excellent in handling onto a testing apparatus, it is possible to perform a predetermined test accurately and quickly without special technique or complicated and tedious operation.

The microchip 50 is the same as what is called, in general, an analysis chip, micro reactor chip or the like. The testing chip is made of, for example, resin, glass, silicon or ceramics, and formed with a micro flow path having a size of micron order such as approximately 10 to several 100 μm in width and height. The literal and longitude sizes are usually several ten millimeters and height is several millimeters in height.

In the above described chip, liquids in the respective storage sections, such as regent storage sections for respective reagents and a specimen storage section, are fed by the above described micro pumps which are communicating with these respective storage sections via a pump connecting section 64 having flow path openings to communicate with the micro pumps.

Preferably, elements other than the testing microchip 50 are integrated as the system main body 10, and the testing microchip 50 is attachable and detachable to and from the system main body. It is possible to provide micro pumps in the testing microchip 50, however, plural micro pumps are integrated to the system main body. A micro-pump unit including these plural micro pumps and a chip connecting section having flow path openings to communicate with the testing chip is disposed in the base main body of the system main body. As shown, the testing microchip 50 is mounted on the system main body, and the pump connecting section of the testing microchip 50 is connected with the port of the chip connecting section of the micro pump unit of the system main body by superimposing the surfaces on each other.

A target value of flow rate is set on the device for electric control system to control a micro pump and a driving voltage corresponding to it is supplied to the micro pump. A control device in charge of such a control also may be integrated in the main body of a system in accordance with the invention, as described later, to have the control device perform control of operation when connecting the pump connecting section of the testing chip with the chip connecting section of the micro pump unit of the system main body.

In the detection processing device which is a unit in charge of optical detection, and collection and processing of data, the means for optical measurement is not particularly limited if a method, such as visible spectroscopy or fluorescent photometry, is applied. However, an LED, photomultiplier tube, photodiode, CCD camera and the like are preferably provided, as necessary, in the system main body.

At least, a control deice to control the functions of the micro-pump unit and the detection processing device is incorporated in the system main body of a system in accordance with the invention. The control device may further integrally control the system, including temperature control, recording and processing of measured data. In the control device in this case, various conditions having been set regarding the order, capacity, timing of liquid feed, etc. are incorporated into software mounted on an analysis system, as contents of a program as well as the control of micro pumps and temperature. Pre-processing of a specimen being a measurement sample and a serial analysis process including reaction and detection are performed in a state where the chip is mounted on the system main body 10 in which the micro pumps, detection processing device and the control device are integrated. Analysis may be started after charging a sample into a mounted chip or after mounting a chip in which a sample has been charged on the system main body. Preferably, a predetermined reaction and optical measurement, based on feeding of the sample and reagent, pre-processing and mixing, are automatically executed as a serial continuous process, and measured data is stored in a file as well as necessary conditions and recording items.

With an analysis chip of a prior art, when performing a different analysis or synthesis, it is necessary to prepare a micro fluid device each time, corresponding to a changed content. On the other hand, in a micro integrated analysis system in accordance with the invention, it is only necessary to replace the above described chip that is attachable and detachable. When it is necessary to change the control of the respective flow path elements, the change can be made by modifying the control program stored in the system main body.

(Testing Chip)

In a testing microchip 50 used in a system in accordance with the invention, respective flow path elements or structures are disposed at positions suitable for functions, by a micro processing technology, so that the chip can be used for various tests, processing and separation of samples, chemical synthesis, etc. As fluid storage sections in the testing microchip 50, there are provided a specimen storage section to store specimen solution and a plurality of reagent storage sections to store respective reagents. In these reagent storage sections, there are stored reagents, cleaning liquid, denaturation solution, and the like to be used for a predetermined reaction. This is because it is desirable that reagents are stored in advance so as to perform a test quickly regardless of time and place. Regarding reagents or the like incorporated in the chip, the surfaces of reagent sections are processed for sealing so as to prevent evaporation, leakage, entrance of gas bubbles, contamination, denaturation, etc.

By the use of a basic substrates, namely, a groove formed substrate and a covering substrate, a preferable structure in a testing chip in accordance with the invention is formed with a pump connecting section, valve base sections, liquid reservoir sections (respective storage sections such as a reagent storage section and specimen storage section, and waste liquid reservoir section), liquid feed control section, reverse flow protection section, reagent quantation section, mixing section, etc., and also formed with a flow path, at least, on the grooved substrate. Herein, the covering substrate covers in tight contact, at least, these structures, the flow path and the detection section. At least, the detection section is covered with a light transparent covering substrate in tight contact.

The basic structure of the testing chip is arranged typically by a proper combination of one or more forming materials, for which various forming materials are applicable and used depending on the chartacteristics of the individual materials. For example, fluorocarbon resin, such as polystyrene, polyethylene, polypropylene, a polyvinyl chloride, polycarbonate, and polytetrafluoroethylene, polysiloxane based polymers, such as poly dimethyl siloxane, Polyolefin based polymers, such as polymethylmethacrylate, polyvinyl alcohol, and an ethylene-vinylalcohol copolymer, polyester based polymers, such as a polyethylene terephthalate and a polybutylene terephthalate, polyamide based polymers, such as 6-nylon, 6, and 6-nylon, annular cycloolefin resin, polyarylate resin, a cellulose based polymer like a cellulose acetate or a cellulose nitrate, a various inorganic matter glass, silicone, ceramics, a metal, etc. are may be listed. In particular, polysiloxane based polymers, such as polystyrene, polyethylene, polypropylene, a polyethylene terephthalate, polymethylmethacrylate, a polyvinyl chloride, polycarbonate, and poly dimethyl siloxane, silicone, and a glass especially may be preferable. However, the invention is not limited by these examples indicated.

As described above, although the selection of materials is wide, a material is desired to be workable, durable against reagents, heat resistant, and inexpensive. Since there is no single material that meets all these requirements, it is necessary to properly select chip material, taking the structure, purpose, detection method, etc. of a chip into account. Further, chips by a combination of plural materials are also produced. Chips for an object of a number of measurement specimens, particularly clinic specimens having a possibility of contamination and infection, are preferably disposable and flexible for multipurpose and mass-producible.

From the above-described point of view, the flow path, flow path elements and body of a testing chip which is used in a system in accordance with the invention is formed of plastic resin that is mass-producible, light weighted and easy to be burned and disposed so that the chip is easy to be produced and disposable. The resins used are preferably desired to have satisfactory characteristics of workability, anti-water absorbing, chemical resistance, heat resistance and inexpensiveness. Polystyrene type resins are preferable for a grooved formed substrate, because polystyrene is excellent in transparency, mechanical characteristics and formability and easy for micro processing. By using plastic material having more of these characteristics, it is possible to produce a chip with a fewer members that construct the chip and the processing and manufacturing process can be made simple.

In case it is needed to be heated up to around 100° C. due to the requirement of analysis, the material needs to be replaced with a material excellent in heat resistance, for example, polycarbonate, polyimide, polyether imide, poly Benz imidazole, or polyetheretherketone.

To promote reaction of alanyte, often a predetermined portion of a flow path or a reaction part in micro reactor is heated up to a predetermined temperature. In a heated area to be heated, the temperature of spot heating is usually up to around 100° C. On the other hand, in the case of a specimen that becomes unstable at high temperature, the reagent is forced to be cooled. Considering such rise and fall of the temperature of a local area in the chip, a material of adequate thermal conductivity is selected preferably. For such materials, resin material and glass are given. By forming these areas with a material having a small thermal conductivity, spreading of heat on the surface is controlled and solely the heated area can be selectively heated.

To detect fluorescent matters or products of color reaction optically, the detecting portion which covers, at least, the detecting part of the micro flow path on the surface of the testing microchip needs to be a light transparent member. Therefore, for the light transparent covering substrate, transparent materials, such as alkali glass, quartz glass and transparent plastics, can be used. The covering substrate as a transparent plate, is adhered on the groove-formed substrate so that it is formed to cover at least these structural sections, the micro flow path and detecting section. Herein, such a covering substrate may be a type that covers the entire top surface of the chip.

(Micro Flow Path)

Figure 7:
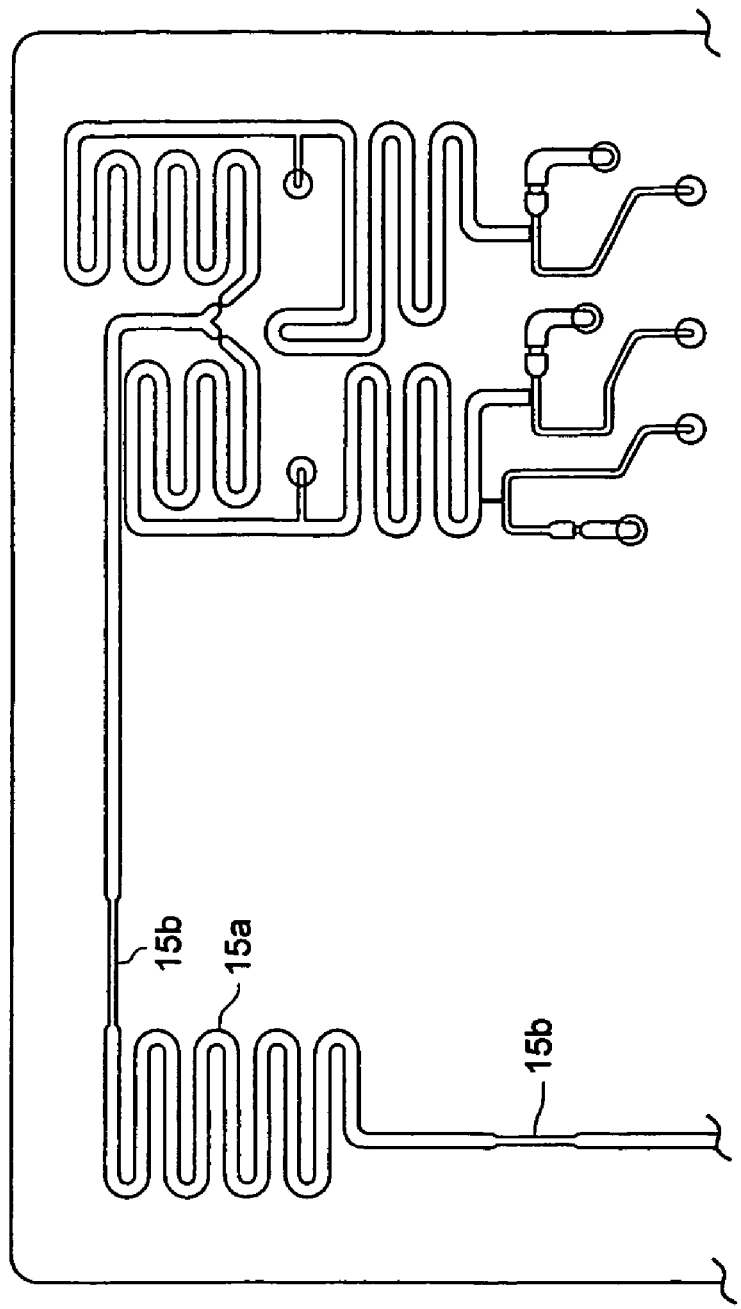
FIG. 7 is a diagram showing a structure in which micro flow paths communicating with the ends of the flow path of the heating section are narrower than flow paths before and after them, wherein the diagram shows only a part of a flow path system of the testing chip.
Figure 9A:
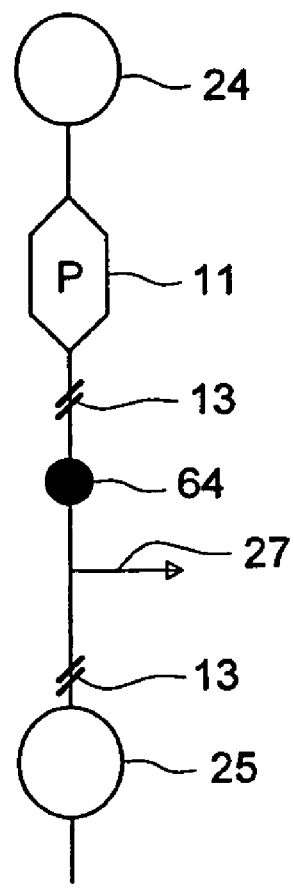
FIGS. 9A and 9B are diagrams showing a structure of a periphery of the pump connecting section of a chip in a case where a piezo pump and the chip are separated from each other.
Figure 9B:
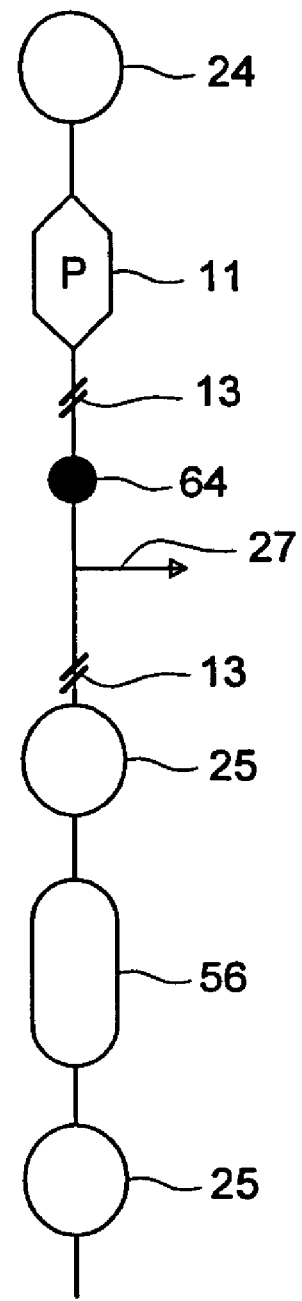

The flow path of the testing chip as a micro reactor is formed on the substrate in accordance with flow path disposition designed in advance according to a purpose (FIGS. 7, 9A and 9B). The micro flow path in which liquid flows is a micro flow path with a micrometer order width formed to have a width of several ten to several hundred µm, preferably 50 to 100 µm, and a depth of about 25 to 200 µm, preferably 50 to 100 µm. If the width of flow path is smaller than 50 µm, flow path resistance increases and it is inconvenient for fluid feeding and detection. In a flow path with a width exceeding 500 µm, the advantage of the micro scale space is reduced. The forming method is based on a microprocessing technology of a prior art. Typically, transferring of a micro structure using photosensitive resin through photolithography technology is preferred. Using the transfer structure, elimination of unnecessary parts, adding of necessary parts and transferring of shapes are carried out. After making a pattern, which forms the constructive elements of the chip by photolithography technology, the pattern is transformed onto resin. Therefore, for the material of the basic substrate on which the minute flow path of the micro chip is formed, plastic that can transfer sub-micron structure accurately and is excellent in mechanical characteristics is preferably used.

Polystyrene, polydimethylsiloxane, etc. are excellent in shape transferring. Injection molding and extrusion molding may be utilized, if necessary.

(temperature control of a predetermined part of a micro flow path of a testing chip)

Figure 3:
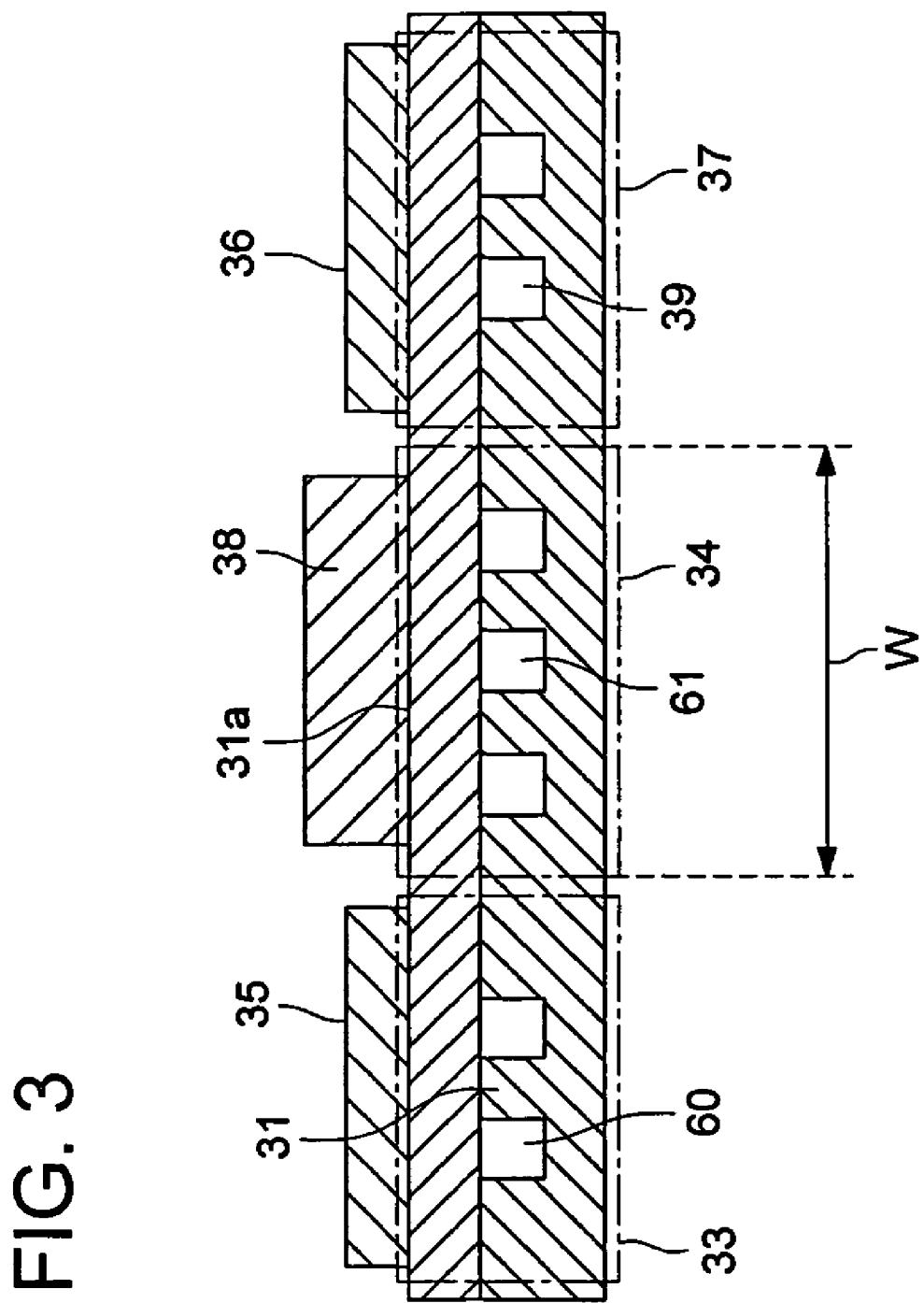
FIG. 3 is a cross-sectional view of the periphery of a reaction flow path and a reagent mixing flow path of a testing chip in an embodiment of a micro integrated analysis system, and a heating member, heat dissipating member and a cooling member which are in contact with the surface of the chip.
Figure 4:
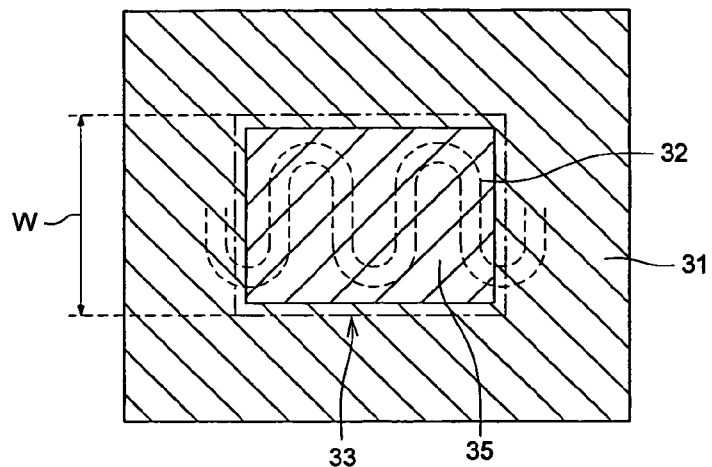
FIG. 4 is a top view of the periphery of a heated area, to be heated, of the chip by the heating member.

Referring to FIGS. 3 and 4, a preferable embodiment of temperature control of the micro flow path of a chip in a micro integrated analysis system in accordance with the invention will be described below.

An embodiment where a heated area to be heated and a cooled area to be cooled are provided both on the same chip is not a rare embodiment of a chip for biological material analysis. It is because, normally, a specimen and reagent is desired to be cooled, and on the other hand, while high temperature is necessary for detection and reaction. An example of a micro flow path that is included in a temperature adjusting area and selectively heated can be a flow path that constructs a reaction part for reaction between a target material and reagent. A concrete example of reaction in a flow path that constructs a reaction part is gene amplification reaction of analyte and reagent by a PCR method. Further, an example of a micro flow path that is included in a temperature adjusting area and selectively cooled can be a specimen storage section, a reagent storage section and/or a flow path for making plural reagents meet and get mixed with each other. In this case, reagent for gene amplification reaction can be an example of the above described reagents.

In the present invention, a heat generator or a thermal conductive member connected with a heat generator or the like to be in contact with a chip surface in a heated area that contains a flow path part is set to be selectively heated, the chip being formed with a serial flow path, so as to heat the heated area. Further, a cooling body or a thermal conductive member connected with a cooling body or the like is set to be in contact with a chip surface in a cooled area that contains a flow path part to be selectively cooled, so as to cool the cooled area. Such heated and cooled areas are set under temperature control in the system, as a temperature control area of the testing chip.

FIG. 3 is a cross-sectional view of the periphery of a reaction flow path and a reagent mixing flow path of a testing chip in an embodiment of a micro integrated analysis system, and a heating member, heat dissipating member and a cooling member which are in contact with the surface of the chip. In the present embodiment, respective members related to temperature control by the control section provided in the system main body are disposed on the respective micro flow paths having different functions, in order to perform selective heating, cooling and heat release of the respective areas. That is, a heating member 35 is pressed against a heated area 33 including a reaction section flow path 60, so as to heat the area to a predetermined temperature; a heat releasing member 38 is pressed against a non-heated area 34 including a different flow path 15, so as to keep the area at a normal temperature; and a cooling member 36 is pressed against a cooled area 37 including a reagent mixing flow path 39 in which reagents are mixed so as to cool the area to a predetermined temperature.

In the present embodiment, the heating member 35 is pressed against the chip surface 31a in the heated area 33 (the chip area, enclosed by a chain line) that includes the reaction flow path 60 which is a micro flow path to perform reaction between a specimen or a biological material (for example, a DNA or another biological material) extracted from a specimen and reagent, a gene amplification reaction, for example, so that the heated area 33 is locally heated (FIG. 4). In the heated area 33, the chip thickness T is preferably not greater than a half of the width W in the chip surface direction thereof. Thus, heat from the heating member 35 spreads enough in the thickness direction in the heated area 33, and heating can be carried out to a predetermined temperature uniformly without a temperature gradient.

In FIG. 4, the heating member 35 is pressed against the chip surface 31a by mounting the testing chip on the system main body. The heating member 35 may be a heat generator (heater) in a sheet form that causes a resistance to generate heat with a current and transfers heat directly or through a dielectric body, a member with a high thermal conductivity, for example, a metallic member such as aluminum, which is connected to the heater and is kept in contact with the chip surface 31a on its surface, and a Peltier element. The heating member 35 may be disposed on both the surfaces of the chip 31, if necessary for uniform heating or quick rise in temperature of the heated area 33.

The heating member 35 is provided with a temperature sensor, and the current through the heating member 35 is controlled, according to a temperature measured by the temperature sensor. Further, the temperature sensor is connected to a controller having a memory that stores a control program related to heating operation, and the controller controls a power supply circuit connected to the heating member 35, according to the program. The heating temperature in the heated area 33 is, for example, approximately up to 100° C.

In such a manner, it is possible to perform selective and uniform heating and cooling at the respective plural function parts on the serial micro flow path formed in the testing chip.

The structure in the present embodiment is used for analysis of a specimen or a biological material extracted from a specimen, and preferably used for performing gene amplification reaction by a PCR method. The structure is suitable for a PCR method, because quick rise in temperature, concretely from approximately 40° C. to 90° C., and frequent repeat of rise and fall in temperature is required.

(Temperature Distribution Control)

In bioassay including a PCR method and synthesis reaction, unrigorous thermal conditions may often affects the success of reaction and cause problem with the control of reaction. For example in PCR, it is required to exactly control, not only thermal conditions, but also the heating time period. If there is an intermediate temperature area in a flow path in a reaction section, non-specific amplitude is caused as a side-reaction, which inhibits amplification of a target sequence. Consequently, it is possible that amplification reaction, which is an object, may not occur enough. Therefore, the temperature difference between a flow path at a reaction section where gene amplification or the like is performed and the both end portions thereof is preferably rigorous. This is advantageous also from a viewpoint of prevention of losing reagent, specimen and mixed solution of them from a flow path. Loss of liquid from a micro flow path due to evaporation or the like is caused in such a manner that the air enclosed between the surface of the chip and the system main body, which are in tight contact, expands and turns into bubbles to raise the flow path pressure in a flow path, thereby pushing out the liquid. Further, it is assumed that when air gets out, reagent or the like enters the gap created between the surfaces in tight contact, and the reagent or the like leaks out from there. Still further, the generation of bubbles from inside the liquid in the heated area or the vicinity thereof is also relates to loss of liquid in the flow path and generation of troubles due to such bubbles.

In the temperature adjusting area on the micro flow path, as long as heat transfer between the heated area and the surrounding area thereof is effectively insulated from the heating side by a heat insulating device and heat is exactly tightly insulated without generation of a temperature gradient between them, there is little intermediate temperature area that is present on the flow path. With such temperature adjusting, it is possible to well prevent an outer flow path neighboring a predetermined temperature adjusting area from being heated.

With a micro integrated analysis system in accordance with the invention, an embodiment of a heat insulating device is not particularly limited, however, any one of the following or a combination is preferable.

As a heat insulating device, from a heating side, for the both end portions of a micro flow path area that is selectively heated, a member which cools the both end portions can be employed, first. Such a cooling member is made in contact with the both end portions, as shown in FIG. 3. A Peltier element is preferable as the cooling member 36 (FIG. 3). The Peltier element may be provided with a heat sink in contact to dissipate the heat. Further, a member with a high thermal conductivity, such as a block of a metallic member of aluminum or the like, may be used together. A cooling member 36 may be disposed on the both surfaces of the chip 31, if necessary for uniform cooling or quick fall in temperature of the cooled area 37.

Figure 5:
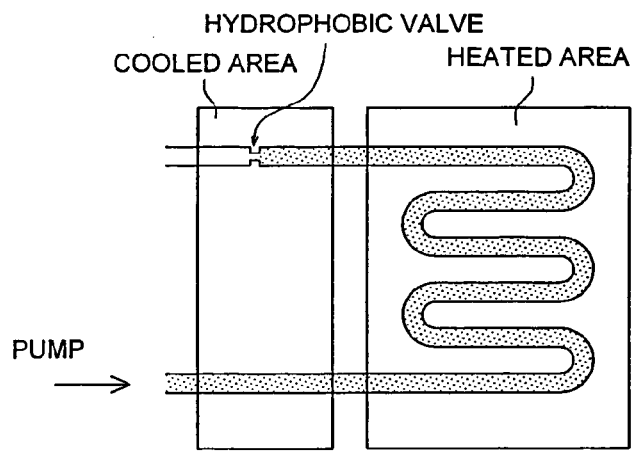
FIG. 5 shows a solution to prevent evaporation of liquid meniscus that is ahead of the heated area and generation of vapor from inside the liquid in the heated area.

One of concrete parts which require such cooling is the vicinity of a heated area in case of heating a portion of a liquid in a flow path, particularly the meniscus of liquid which is a head. Namely, in the case of feeding liquid to a successive reaction process section after completing a heating process of the liquid at a heating section, it is necessary to keep the liquid where it is in the heated area for a certain time. In this situation, it is necessary to cool the meniscus of the liquid in the flow path to a predetermined temperature or lower to prevent evaporation of the liquid from the meniscus and a trouble as described above. To solve this problem, as shown in FIG. 5, it is preferable to provide "a hydrophobic valve" in the cooled area and take steps as described below.

(1) Ahead of a heat insulating area (cooled area) or in the cooled area, there is a hydrophobic liquid stopper (hydrophobic valve) and the meniscus is stopped at the hydrophobic valve at the time of heating the liquid.

(2) In the above (1), further, a pressure is applied to the liquid by a micro pump at the time of heating the liquid, wherein the pressure is large enough to prevent the liquid from leaking from the hydrophobic valve.

Figure 6:
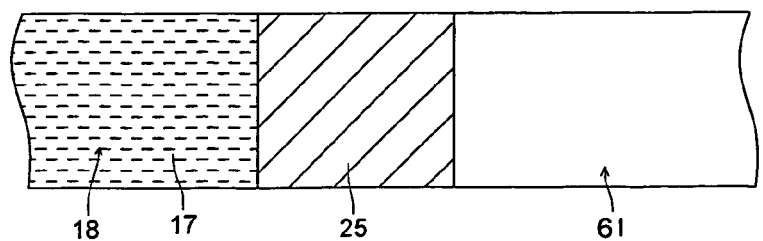
FIG. 6 is a diagram showing a reagent storage section and a sealing agent for sealing a reagent in the reagent storage section, wherein the agent is used as heat insulating oil that insulates the both ends of a flow path of a heating section (for example, a reaction section) from heat of the heating section.

As another embodiment of a heat insulating device to insulate the both end portions of a micro flow area to be selectively heated, against the heating side, there is an embodiment in which heat transfer from the heating side is insulated by heat insulating oil that is charged in the micro flow path at the both end portions (FIG. 6). For such heat insulating oil, oil that is the same as a sealing agent for sealing reaction reagent in a reagent storage section until the time of use is preferable (FIG. 6). The sealing agent may be of any material that is plastic and insoluble with water, and is preferably an oil with a water solubility not greater than 1% and a melting point in a rage 8° C. to ambient temperature (approximately 25° C.). Such an oil is in a solid state during storage to seal reagent, and turns into flowing state at the time of use so as to easily flow out the reagent from a flow path that is communicating with the reagent storage section. Concrete examples of oils are described in the following table. It is also preferable to flow the same oil after specimen solution or specimen processing solution to be fed. By sandwiching both ends of a flow path in a reaction section with one of these sealing agents as heat insulating oil, uniform heating of reaction mixed solution (namely, specimen solution and reaction reagent) and insulation of heat transfer to the periphery will be attained. The heat insulating oil may be supplied from an oil stocker. The oil stocker is attached to the system main body, and at the time of testing, oil is fed out by a micro pump to be charged into the above described micro flow path area that is selectively heated in the testing chip, for example, into the micro flow path at the both end portions of the reaction section.

TABLE 1

| Cmposition Name | Melting point (° C.) | |
| --- | --- | --- |
| Pentadecane | 9.9 | |
| Tridecylbenzene | 10 | |
| Propyl phenyl ketone | 11 | |
| 1-Heptadecene | 11.2 | |
| Pentadecyl acetate | 11.4 | |
| Ethyl myristate | 12.3 | |
| Pelargonic acid | 12.5 | |
| 2-Methylundecanoic acid | 13 | |
| Caproic acid | 14 | 15 |
| Decane-2-one | 14 | |
| Ethyl pentadecanate | 14 | |
| 5-Methyltetradecanoic acid | 14.5 | 15 |
| 12-Tridecenol-1 | 15 | |
| 6-Methyltetradecanoic acid | 15 | 15.5 |
| Undecane-2-one | 15 | |
| 7-Methyltetradecanoic acid | 15.5 | 16 |
| Undecane-1-ol | 15.9 | |
| Didecyl ether | 16 | |

TABLE 1-continued

| Cmposition Name | Melting point (° C.) | |
| --- | --- | --- |
| Tetradecylbenzene | 16 | |
| Ethyl ricinoelaidate | 16 | |
| Pentadecyl caproate | 16.3 | |
| Heptyl phenyl ketone | 16.4 | |
| 10-Methyltetradecanoic acid | 16.5 | 17 |
| Monoheptyl phthalate | 16.5 | 17.5 |
| Caprylic acid | 16.7 | |
| Tridecane-2-ol | 17 | |
| Hexyl phenyl ketone | 17 | |
| 1-Octadecene | 17.6 | |
| 2-Heptylundecanoic acid | 18 | 19 |
| Corfn Cayani | 18 | 24 |
| Hexadecane | 18.2 | |
| Butyl palmitate | 18.3 | |
| 11-Methytetradecanoic acid | 18.5 | 19 |
| Hexadecyl acetate | 18.5 | |
| Methyl pentadecanate | 18.5 | |
| Methyl myristate | 18.5 | |
| Ethyl phenyl ketone | 19 | 20 |
| Amyl palmitate | 19.4 | |
| Methyl oleate | 19.9 | |
| Csrcal resin | 20 | 23 |
| Csm resin | 20 | 30 |
| Glycerin | 20 | |
| Dodecane-2-one | 20 | |
| Coconut oil | 20 | 28 |
| Propyl palmitate | 20.4 | |
| Methyl tridecanate | 20.5 | |
| Methyl phenyl ketone | 20.5 | |
| 11-Methyloctadecanoic acid | 21 | |
| Dodecyl laurate | 21 | |
| Monooctyl phthalate | 21.5 | 22.5 |
| Heptadecane | 21.9 | |
| Babassu oil | 22 | 26 |
| Pentadecylbenzene | 22 | |
| Methyldocosanoic | 22 | |
| acidOctyl palmitate | 22.5 | |
| Heptane-1,7-diol | 22.5 | |
| 2-Butyltetradecanoic acid | 23 | 24 |
| 1-Nonadecene | 23.4 | |
| Dodecane-1-ol | 24 | |
| Heptadecyl acetate | 24.6 | |

Still another preferable embodiment of heat insulating of the both end portions of the micro flow path area to be selectively heated is narrow flow paths having a smaller cross-sectional area arranged at the both end portions of the micro flow path. Specifically, as shown in FIG. 7, the cross-sections, of the micro flow path, near the inlet and outlet of the micro flow path area to be selectively heated are arranged to be narrower than the cross-sections of the micro flow path therebetween. The extent of narrowing is not greater than ¾ of the cross-sectional area of the micro flow path therebetween and preferably not greater than ⅔, wherein the narrowed cross-sectional area preferably has a width and depth not smaller than 50 μm, considering the flow path resistance. More specifically, the ratio is preferably 1/10 to ¾, and more preferably ⅓ to ⅔, regarding the flow path cross-sectional area. The lengths of the narrow portions of the flow path are individually designed, taking the disposition thereof in the chip and material. Thus, the efficiency of thermal conductivity through the flow path is lowered, substantially obtaining a heat insulating effect.

As an embodiment of a heat insulating device for the both end portions of the micro flow path to be selectively heated, which is applicable as a combination with any one of the above described embodiments, and also as another embodiment applicable alone, the above described both end portions and at least a part of the non-heated area 34 neighboring them are preferably formed of a material with a comparatively small thermal conductivity (not greater than 10 W/m·K, and preferably not greater than 2 W/m·K). Such materials include resin material and glass material. By employing a material having a small thermal conductivity to form these areas, heat transfer in the surface direction is inhibited and only a predetermined temperature adjusting area is selectively heated, attaining a substantial heat insulating effect.

The micro integrated analysis system is used by a method, in accordance with the invention, that insulates the both end portions of the micro flow path area that is on the micro flow path provided in a testing chip for analysis of a target material in a specimen and is selectively heated, against heat from the heating side, in any one or more of the following manners. That is, forming at least the both end portions, described above, of the chip with a material having a thermal conductivity not greater than 10 W/m·K; cooling the both end portions by making a cooling member in contact with them; charging heat insulating oil in the flow path at the both end portions; or making the cross-sectional areas of the flow path at the both end portions narrower than those of the flow paths after and before.

(Micro Pump Unit)

The system main body 10 in accordance with the invention includes a micro pump unit as a component that has a chip connecting section with flow path openings to communicate with the testing chip and has a plurality of micro pumps.

Figure 8A:
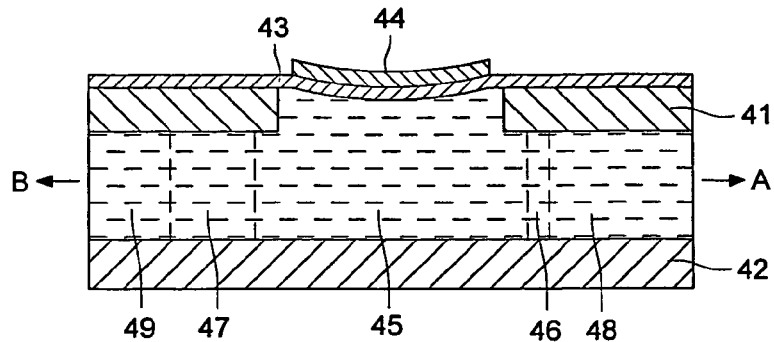
FIG. 8A is a cross-sectional view showing an example of a piezo pump.
Figure 8B:
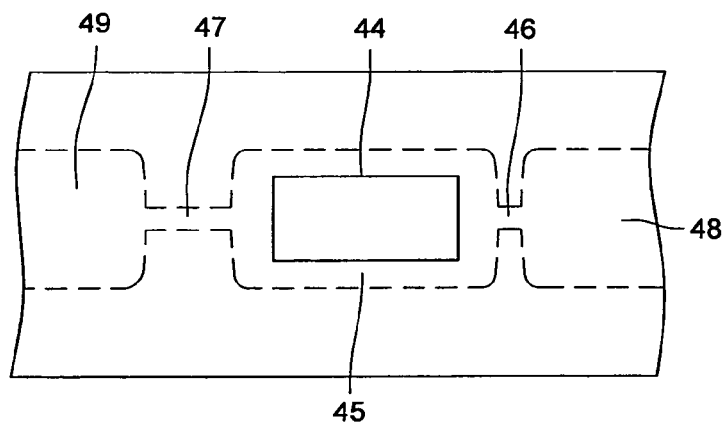
FIG. 8B is a top view of the pump.

Regarding micro pumps, for example, plural micro pumps may be incorporated in the system main body 10, as a pump unit in a chip form that is formed by a photolithography technology or the like. For a micro pump, various types can be used, including a check valve type pump provided with a check valve in an inlet and outlet hole of a valve chamber with an actuator, however, a piezo pump is preferably used. FIG. 8A is a cross-sectional view showing an example of a piezo pump, and FIG. 8B is a top view thereof. On this micro-pump, there are provided substrate 42 on which a first liquid chamber 48, first flow path 46, pressing chamber 45, second flow path 47 and second liquid chamber 49 are formed, upper substrate 41 laminated on the substrate 42, vibration plate 43 laminated on the upper substrate 41, piezoelectric element 44 laminated on the side facing the pressing chamber 45 of the vibration plate 43 and a driving section (not shown) for driving the piezoelectric element 44. This driving section and two electrodes on the surface of the piezoelectric element 44 are connected by wiring with a flexible cable or the like, and a driving circuit of the driving section applies a voltage in a specific waveform to the piezoelectric element 44 via this connection.

In this example, photosensitive glass substrate having a thickness of 500 μm is used as substrate 42, and first liquid chamber 48, first flow path 46, pressing chamber 45, second flow path 47 and second liquid chamber 49 are formed by conducting etching to the depth of 100 μm. A width of the first flow path 46 is 25 μm and a length is 20 μm. A width of the second flow path 47 is 25 μm and a length is 150 μm.

A top face on each of the first liquid chamber 48, first flow path 46, second liquid chamber 49 and second flow path 47 is formed by laminating the upper substrate 41 on the substrate 42. A portion on pressing chamber 45, corresponding to the top of the pressing chamber 45 is processed by means of etching to become a through hole.

On the top surface of the upper substrate 41, there is laminated vibration plate 43 composed of a 50 μm-thick thin sheet glass, and piezoelectric element 44 composed of a 50 μm-thick lead titanate zirconate (PZT) ceramics is laminated on the vibration plate 43.

The piezoelectric element 44 and the vibration plate 43 attached on the piezoelectric element 44 are vibrated by driving voltage coming from a driving section, and thereby a volume of the pressing chamber 45 is increased or decreased. The first flow path 46 and the second flow path 47 are the same in terms of a width and a depth, and a length of the second flow path is longer than that of the first flow path, and when the pressure difference grows greater in the first flow path 46, a turbulent flow is generated to flow in whirls at the inlet and outlet and the surroundings, and flow path resistance is increased. On the other hand, in the second flow path 47, even when the pressure difference grows greater, a laminar flow still stays because a flow path length is greater, thus, a rate of change of flow path resistance for a change of pressure change is small, compared with the first flow path.

For example, when vibration plate 43 is moved quickly toward the inside of the pressing chamber 45 by driving voltage for the piezoelectric element 44 to decrease a volume of the pressing chamber 45 while giving a large pressure difference, and then, when vibration plate 43 is moved slowly toward the outside of the pressing chamber 45 while giving a small pressure difference to increase a volume of the pressing chamber 45, a fluid is fed in the direction B in the same drawing. On the other hand, when vibration plate 43 is moved quickly toward the outside of the pressing chamber 45 to increase a volume of the pressing chamber 45 while giving a large pressure difference, and then, when vibration plate 43 is moved slowly toward the inside from the pressing chamber 45 while giving a small pressure difference to decrease a volume of the pressing chamber 45, a fluid is fed in the direction A in the same drawing.

Meanwhile, a difference of a rate of change of flow path resistance for a change of pressure difference between the first flow path and the second flow path does not need to be caused by a difference of a flow path length, and it may also be one based on another difference in shapes.

With a piezo pump structured as described above, feeding direction and speed of a desired fluid can be controlled by varying the driving voltage and frequency of the pump. Though not shown in FIG. 8A or 8B, the first liquid chamber 48 is provided with a port 72 connected with the driving liquid tank 10, and the first liquid chamber acts as "a reservoir" to receive supply of driving liquid from the driving liquid tank 30 via the port 72. The second liquid chamber 49 forms a flow path of the micro pump unit 26, and a port 73 is provided ahead of the flow path to be connected with the "pump connecting section" 12 of the testing chip.

Figure 8C:
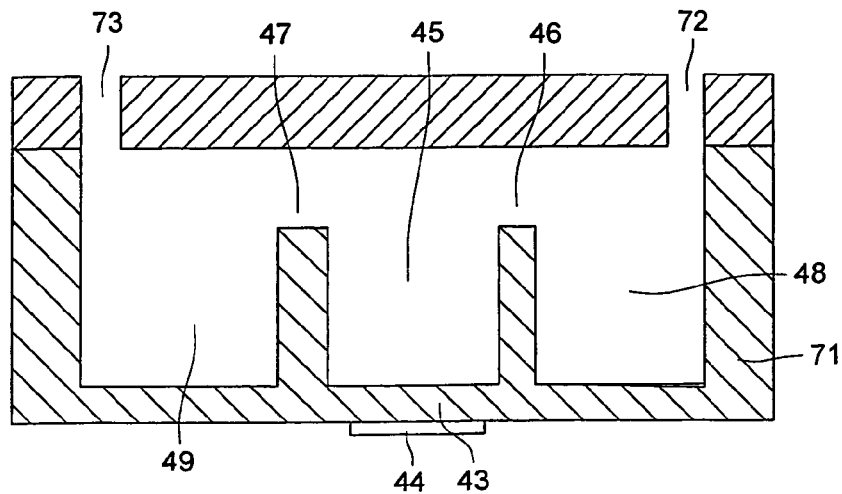
FIG. 8C is a cross-sectional view showing another example of a piezo pump.

FIG. 8C shows another example of this type of pump. IN this example, the pump is structured with a silicon substrate 71, a Peltier element 44, and a flexible wire, not shown. The silicon substrate 71 is produced by processing a silicon wafer with a photolithography technology into a predetermined shape and formed with a pressing chamber 45, diaphragm 43, a first flow path 46, a first liquid chamber 48, a second flow path 47 and a second liquid chamber 49. The liquid chamber 48 is provided with a port 72 and the second liquid chamber 49 is provided with a port 73. Herein, in the case of, for example, separating a piezo pump from the testing microchip 50, shown in FIG. 1, the piezo pump is communicating with the pump connecting section 64 of the testing microchip 50 via the port 73. For example, it is possible to connect a pump with the testing microchip 50 by superimposing a substrate 74 thorough which the ports 72 and 73 are formed and the vicinity of the pump connecting section of the testing chip on each other. Further, as described above, it is also possible to form plural pumps in a single silicon substrate. In this case, ports which are on the side of the substrate opposite to the ports connected with the testing microchip 50 are preferably connected with a driving liquid tank 30. If there are plural pumps, those ports may be connected with a common driving liquid tank.

The relationship between the micro pumps, as described above, and the system in accordance with the invention, shown in FIG. 1, will be described below. In the example in FIG. 1, the micro pumps belong to the system main body, as devices separate from the testing microchip 50, and are communicating with the driving liquid tank. When the micro pumps and the testing micro chip 50 are jointed to each other in a predetermined form, the ports 73 of the chip connecting section of the micro-pump unit 26 are connected to the pump connecting section 64 that belongs to the testing chip and has flow path openings, to communicate with the flow paths of the testing chip.

FIGS. 9A and 9B show structures in the periphery of the pump connecting section of a testing microchip 50 in the case of arranging a piezo pump, as a micro pump, to be separate form the testing microchip 50. In the Figure, the flow path on the downstream side from the pump connecting section 64 which communicate from the port of the micro pump for feeding out liquid to the flow path of the testing chip is on the testing chip. FIG. 9A shows the structure of a pump section to feed driving liquid and FIG. 9B shows the structure of a pimp section to feed reagent. Herein, the reference numeral 24 denotes the storage section of the driving liquid, which corresponds to the driving liquid tank in FIG. 1. The driving liquid may be any one of oil types, such as mineral oil, and water types. The reference numeral 25 denotes the storage section for sealing liquid that seals reagent that is stored in advance. This sealing liquid serves to prevent the reagent from reaction when it leaks into a micro flow path. The sealing liquid is in a solid or gel state under refrigerating condition for storage of the testing chip before the time of use, and melts and turns into a flowing state when the temperature becomes the ambient temperature. The sealing liquid may be charged into a micro flow path or into a reservoir section provided for the sealing liquid.

As another embodiment, it is also possible to incorporate a micro pump into the testing chip. This embodiment is applicable particularly in a case where the flow path on a chip is comparatively simple and the chip is for an object or purpose that assumes repeated use, for example, a testing chip for chemical synthesis reaction.

(Example of a Testing Chip)

The testing chip has, for example, a rectangular plate shape with dimensions 50×76×3 mm, and is preferably made of an elastic material having a self-sealing characteristic and transparent or translucent, at least, at the detection section. Such a chip having self-sealing characteristic comes in tight contact with a surface of a glass substrate or the like just by being put thereon. For a material of such a chip, for example, PDMS (Polydimethylsiloxane) that is a kind of silicon rubber is used.

The testing microchip 50 is formed with a pattern of a micro flow path for analysis or chemical synthesis. An example of the dimension and shape of a micro flow path is a groove with a rectangular cross-section with a width of approximately 100 μm and a depth of approximately 100 μm. In the testing chip, there are provided a pump connecting section, micro flow path, specimen storage section, reagent storage section, liquid feed control section, reaction section, detection section, etc., and they are connected through a flow path. Further, in order to increase the accuracy of liquid feeding, a reverse flow check section, liquid quantitation and feeding mechanism, or the like are preferably arranged. It is also possible to adopt various structures and materials other than those described above.

(Example of Analysis)

The testing chip used for the micro integrated analysis system in accordance with the invention is one formed with a serial micro flow path and can be subjected to the following processing:

The testing chip is mounted into the base main body in a state where the pump connecting section of the testing chip and the chip connecting section of the micro pump unit 26 are in liquid tight contact, then a target material contained in a specimen stored in the specimen storage section or in processed solution for which the specimen has been processed in a flow path and reagent stored in the reagent storage section are fed to a flow path forming a reaction part to mix and react with each other, and thereafter the produced material by the reaction or a processed material thereof is fed to a flow path forming a detection part so as to be detected by the detection processing device.

(Specimen)

A specimen to be an object of measurement in accordance with the invention is a sample containing analyte that originates from a biological body. The specimen itself is not particularly limited, and most samples that originate from, for example, whole blood, blood plasma, blood serum, buffy coat, urine, bowel movement, saliva, sputum, etc. are applicable.

In the case of gene testing, as nucleic acid to be a template for amplification reaction, gene, DNA or RNA is analyte. A specimen can be one prepared or separated from a sample with a possibility of containing such a nucleic acid. Therefore, besides the above samples, cultured cell substance; the samples contain nucleic acid such as virus, bacteria, yeast, the samples contain nucleic acid such as plant and animal; the samples possibly contain or entrain germs, and other samples which may contain nucleic acid are applicable. Technologies in prior arts can be used for the method preparing gene, DNA or RNA from such samples without specific restriction. In the micro integrated analysis system in accordance with the invention, comparing with manual operation using conventional devices, the required amount of specimen is extremely small. For instance, only about 2 to 3 µL of blood is injected to a chip measuring several centimeters in length and in width. For instance, in case of a gene, 0.001 to 100 ng of DNA is to be injected. Therefore, including the case where only a minute amount of specimen can be obtained, testing of a biological body by a system in accordance with the invention is little limited in specimen, and accordingly requires a small amount of reagent, which reduces testing cost.

(Gene Test)

The system in accordance with the invention can be satisfactorily used particularly for gene or nucleic acid (DNA, RNA). In this case, the micro flow path of the testing microchip is structured to be suitable for PCR smplification. Also for biological materials in other cases than gene test, the flow path structure will be almost the same. Normally, a specimen pre-processing section, reagents, probes will be changed, wherein disposition of liquid feed elements and the quantity will be changed. Those skilled in the art can easily change the type of analysis by loading reagent and the like which are necessary for immunoassay, for example, on the testing microchip 50 and making adjustments including a slight modification of flow path element and specification. In this case, the layout and number of the liquid feed elements will be modified. Herein, biological materials other than genes are various metabolism materials, hormones, proteins (including enzyme and antigens), and the like.

In a preferable embodiment of the testing microchip 50, a single chip includes: a specimen storage section charged with a specimen or a biological material (e.g. DNA, RNA, gege) extracted from the specimen; a specimen pre-processing section to perform preprocessing of the specimen; a reagent storage section for storing the reagent used for probe binding reaction and detection reaction (including gene amplification reaction or antigen-antibody reaction); a positive control storage section for storing positive control; a negative control storage section for storing negative control; a probe storage section for storing a probe (e.g. a probe to be hybridized with the gene to be detected, the gene being amplified by gene amplification reaction); a micro flow path communicating with the respective storage sections; and a pump connecting section for connection with separate micro-pumps for feeding a liquid in the storage sections and flow paths.

On the other hand, the testing microchip 50 has a structure as schematically shown in FIG. 10.

That is, the testing microchip 50 is provided with specimen storage section 52 and reagent storage sections 56 in which reagent 58 is sealed in advance.

Plural reagent storage section 56 are provided and each of which is provided with a pump connecting section 64 so as to be connected with a micro pump, shown in FIG. 2, through a pump flow path 51. Each reagent storage section 56 is connected to a reaction flow path on the downstream side through a confluent section 55 which is a Y shape flow path.

The specimen storage section 56 is provided a pump connecting section 64 on the upstream side so as to be connected with a micro pump, shown in FIG. 2, through a pump flow path 51. The specimen storage section 52 is connected, on the downstream side, through plural specimen supply flow paths 53 which are branched from the storage section 52 and respective confluent sections 55 which are U-shaped confluent sections 55, to reaction flow paths 60 and analysis flow paths 61 on the downstream side.

These flow paths 51, 53, 57, 60, etc. are provided with a valve section and the like at a proper position, and is controlled, for example, for quantitation of liquid feeding amount and mixing of the respective liquids.

Further, such a testing microchip 50 is preferably produced as a single chip by a proper combination of more than one members, such as plastic resin, glass, silicon, ceramics.

The minute flow path and the frame of the testing microchip 50 are preferably made of plastic resin that is easy to be processed, inexpensive and easy to be burned and disposed.

For example, polystyrene resin is excellent in formability and tends to adsorb streptavidin, and allows easy forming of a detection part on the micro flow path. The micro flow path is formed to have a width and depth in a range from several ten µm to several hundred µm, for example.

Further, in order to optically detect fluorescent material or a color reaction product, a detection part, at least, that covers the detection part of the micro flow path of the surface of the testing microchip 50 is preferably a transparent member, and more prferably made of transparent plastic.

Reagent 58 stored in a reagent storage section 56 in this way is supplied through a confluent section 55, which is a Y-shape flow path, to a reaction flow path 60 on the downstream side. On the other hand, specimen 54 stored in the specimen storage section 52 is supplied, through the respective specimen supply flow paths 53 branched from the specimen storage section 52 and confluent sections 55 being a Y-shaped flow path, to the reaction flow paths 60 on the downstream side.

Thus, the specimen 54 and the respective reagents 58 are mixed in the reaction flow paths 60, and reaction is started by raising the temperature or in another way. Then, at detection parts provided on analysis flow paths 61 disposed on the downstream side of the reaction flow paths 60, reactions are detected by a detection device 144 structured with an LED 140 that irradiates light and a photodiode 142 that receives light having transmitted.

Herein, as shown in FIG. 3, the reaction flow paths 60 and analysis flow paths 61, which are arranged to be plural separate flow paths, form a reaction and detection system related to positive control and a reaction and detection system related to negative control.

In such a structured micro integrated analysis system 1, the operation is as described below.

That is, specimen solution is injected into the specimen storage section 52 of the testing microchip 50 in which reagents 58 are sealed in advance, and the testing microchip 50 is loaded on the chip conveying tray 22 having been moved in advance to protrude outside the testing chip gateway 14 of the system main body 10.

Thus, the chip conveying tray 22 is taken into the system main body 10 thorough the testing chip gateway 14 to mount the testing microchip 50. In such a manner, the testing microchip 50 is mounted on the system main body and mechanical connection to operate micro pumps for liquid feed is done. Accordingly, when the testing microchip 50 is mounted on the system main body, the testing microchip 50 turns into an operation mode.

The micro pump unit 26 is provided with a plurality of micro pumps, corresponding to the number of parts to be fed with liquid which is pushed out from the upstream side by driving liquid 29. The sections are, for example, the specimen storage section 52, plural reagent storage sections 56, positive control storage section, negative control storage section, etc.

By mounting the testing microchip 50 on the system main body, the micro pumps are connected to the testing microchip 50 via the pump connecting section 64 of the testing microchip 50 so as to function as micro pumps.

The micro pump unit 26 id provided with the plurality of micro pumps and the chip connecting section 66 having flow path openings to communicate with the testing microchip 50.

On the other hand, the testing microchip 50 is provided with the pump connecting section 64 having flow path openings to communicate with the micro pumps, and the pump connecting section 64 of the testing microchip 50 and the chit connecting section 66 of the micro pump unit 26 are brought into liquid tight contact so that the micro pumps are connected with the pomp flow paths 51 and 57.

The pump connecting section 64 of the testing microchip 50 is structured with flow path openings to communicate with the micro pumps and a contact face around them. The chip connecting section 66 of the micro pump unit 26 is structured with flow path openings to communicate with the testing microchip 50 and a contact surface around them.

The contact surface on the micro pump unit side and that of the testing chip side are brought into contact with each other in a state where the flow path openings of the pump connecting section 64 of the testing microchip 50 and those of the micro pump unit side are positioned on each other. In such a manner, the flow path openings of the pump connecting section 64 of the testing microchip 50 and those on the micro pump unit side are connected with each other.

This contact can be achieved by pressing the testing microchip 50 and the micro pump unit 26 against each other. The chip connecting section 66 and the pump connecting section 64 may be provided with, for example, a sealing member of a soft resin, such as Teflon (registered mark), to make the sealing faces of the sealing members be contact faces of the testing microchip 50 and the micro pump unit 26.

In this contact state, as shown in FIG. 2, the driving liquid, for example, oil or buffer solution, that is stored in the driving liquid tank 30 is fed out by micro pumps driven by a pump control device 28.

By supplying the driving liquid 29 from the micro pumps in this way, the reagents 58 stored in the reagent storage sections 56 are supplied through the confluent sections 55 being Y-shape flow paths to the reaction flow paths 60 on the downstream side. On the other hand, the specimen 54 stored in the specimen storage section 52 is supplied through the specimen supply flow paths 53 which are branched into plural flow paths on the downstream side and through the confluents sections 55 being Y shaped flow paths, to the reaction flow paths 60 on the downstream side.

In such a manner, the specimen 54 and the reagents 58 are mixed in the respective reaction flow paths 60 and reactions are started by raising the temperature or in another way. Then, at detection parts provided on the analysis flow paths 61 disposed on the downstream side of the reaction flow paths 60, reactions are detected by the detection device 144 structured with the LED 140 that irradiates light and the photodiode 142 that receives light having transmitted.

Regarding the testing microchip, if the testing microchip 50 is, for example, one that performs amplification reaction by ICAN method (Isothermal chimera primer initiated nucleic acid amplification), a specimen extracted from blood or sputum is stored in the specimen storage section 52.

On the other hand, the reagent storage sections 56 store biotin modified chimera primer which can be specifically hybridized with a gene being the detection object, DNA polymerase having chain substitution activity and reagent containing endonuclease.

Therefore, when the reagents 58 from the reagent storage section 56 and the specimen 54 from the specimen storage section 52 meet with each other through Y-shape flow paths and the like and are mixed with each other in the reaction flow paths 60, it is necessary to promote gene amplification reaction, with heat control at a temperature in a range from 50 to 65° C., and 55° C. for example.

However, heating for a long time causes gas bubbles in the mixed solution of the specimen and reagent, and reagent, for example, biotin modified chimera primer which can be specifically hybridized with a gene being the detection object and the specimen are inhibited from binding with each other due to the gas bubbles, causing a possibility of prohibiting a predetermined test in the testing section.

Further, heating for a long time causes side reactions in addition to reactions between the specimen and reagents, namely side reactions by various materials other than the target material, and the amplified products by the side reactions inhibit amplification of the target material, which makes it difficult to perform analysis by the reaction being a predetermined purpose and the predetermined test may not be executed in the testing section.

Still further, in the case of heating by a heater, even when heating is stopped, it takes a certain time before the heater is cooled down. Accordingly, if the residual heat time before cooling down the heater is long, the above described gas bubbles or side reaction may be created due to affection by the residual heat temperature.

Yet further, the reagents 58 stored in the reagent storage sections 56 have a characteristic to denature affected by temperature. Accordingly, with a long heating time or residual heat time, as described above, it is possible that the reagents 58 stored in the reagent storage sections 56 denature and the predetermined test cannot be executed in the testing section.

Therefore, as shown in FIGS. 2 and 3, there is provided a heating-cooling device 136 that contacts the testing microchip 50 and controls the temperature of the reaction flow paths 60.

This heating-cooling device 136 is structured in such a manner that immediately after the specimen 54 stored in the specimen storage section 52 and the reagents 58 stored in the reagent storage sections 56 meet with each other in the reaction flow paths 60 which are reaction sections, the heating-cooling device 136 heats the mixed solutions of the specimen 54 and reagents 58 and performs reaction processing, and immediately thereafter cools the solutions, under control by a temperature control device 138 based on a built-in program.

Thus, it is possible to perform heating quickly up to a temperature necessary for reaction when the mixed reagent having been mixed and the specimen from the specimen storage section meet with each other in the confluent flow paths and are mixed in the mixing and reaction flow paths.

In such a manner, the heating time can be set to a time period necessary for promotion of reaction, and further, quick cooling is possible. Therefore, no gas babbles are created in the mixed solution of the specimen and reagent, and for example, biotin modified chimera primer which can be specifically hybridized with a gene being the detection object and the specimen are not inhibited from binding with each other by gas bubbles, and thus a predetermined test can be executed in the testing section.

Herein, regarding heating and cooling, cooling is preferably performed during the time after the mixed solution of the specimen and reagent is heated and reaction processing is performed and before side reaction is caused.

Accordingly, the time period to keep heating at a predetermined heating temperature, for example, at 55° C. is different, depending on the kinds of the specimen 54 and reagents 58, and is preferably set to be in a range from 10 to 60 minutes and more preferably in a range from 15 to 30 minutes so that side reaction does not occur and gas bubbles are not created.

The cooling speed (the time period from when cooling starts until the temperature drops near to the ambient temperature) after heating the mixed solution of the specimen 5 and the reagents 58 and performing reaction, as described above, is different, depending on the kinds of the specimen 54 and the reagents 58, and is preferably not longer than 3 minutes and more preferably not longer than 1 minute so that side reaction does not occur and gas bubbles are not created.

Since the heating time can be set to a time period necessary for promotion of reaction, and further cooling can be performed quickly, it is prevented that side reactions other than the reaction between the specimen and reagent, namely, side reactions due to various materials other than a target material occur and amplification products by the side reactions inhibit amplification of the target material. Consequently, it is possible to perform analysis based on reaction as an object, and a predetermined test can be executed in the testing section.

Further, regarding the heating speed for heating the mixed solution of the specimen 54 and reagent 58, as described above, the heating speed (the time from when heating starts until the temperature rises up to a predetermined temperature) for amplification of the mixed solution is preferably as short as possible for prevention of side reaction and for shortening the amplification reaction time, herein the heating speed is preferably not longer than 5 minutes, and more preferably not longer than 2 minutes.

The heating-cooling device 136 is preferably structured with Peltier element that performs heating and cooling, by switching a current.

This Peltier element uses the Peltier effect that is an electric physical effect, and uses the principle that when a voltage is applied on both ends of a jointed different metals, the joint portion performs heating or cooling.

That is, for example, when p type and n type thermoelectric semiconductors are joined together at a copper electrode by a semiconductor that is, for example, produced of an alloy with a chief material of bismath and tellurium, and if a direct current is applied from the n type side, then heat generation occurs in one direction, and if a current is applied from the p type side in the opposite direction, then heat generation occurs in the opposite direction. This principal is used in the above.

In such a manner, using a Peltier element as the heating-cooling device, is it possible to use the heating-cooling device both for heating and cooling by just switching the direction in which the current flows, possible to perform heating and cooling accurately under temperature control, and also possible to downsize the heating-cooling device.

Thus, in the reaction flow paths 60 being a reaction section, immediately after the specimen 54 stored in the specimen storage section 52 and the reagents 58 stored in the reagent storage sections 56 meet with each other, it is possible to heat the mixed solutions of the specimen 54 and the reagents 58, and immediately thereafter, to perform cooling.

In this way, when the specimen 54 stored in the specimen storage section 52 and the reagent stored in the reagent storage section 45 meet and are mixed with each other, it is possible to quickly heat the mixture up to a temperature necessary for reaction with the Peltier element.

Further, when the temperature has become the necessary temperature, it is possible to perform heating for a time necessary for reaction and quick cooling by reversing the direction of the current via the Peltier element so that causing of gas bubbles and side reaction are prevented, thus achieving execution of an accurate test with high accuracy and excellent in reliability.

As described above, since the heating time period can be set to a period necessary for reaction promotion and further quick cooling can be performed, no gas bubbles are created in the mixed solution of the specimen and reagent. For example, biotin modified chimera primer which can be specifically hybridized with a gene being the detection object and the specimen are not inhibited from binding with each other by gas bubbles, and thus a predetermined test can be executed in the testing section.

Still further, since the heating time period can be set to a period necessary for reaction promotion and further quick cooling can be performed, creation of side reactions other than reaction between the specimen and reagents, namely, side reaction due to various materials other than the target material is prevented, and amplification of the target material is prevented from inhibition by amplified products by side reaction. Thus, analysis with reaction as an object can be attained and execution of a predetermined test is achieved in the testing section.

Yet further, it is possible to prevent affection by heating temperature on the reagents stored in the reagent storage section having a characteristic to denature affected by temperature, and thus reagent effects by the reagents can be maintained, allowing execution of a predetermined test in the testing section.

Although in the present embodiment, a Peltier element is used as the heating-cooling device to control the direction in which a current flows to be switched, thereby performing heating and cooling, it is also possible to dispose a heating device 136A and a cooling device 136B, as shown in FIG. 4, neighboring each other as a pair and as the heating-cooling device 136.

With such a structure, the heating device 136A can perform heating and reaction processing of the mixed solution of the specimen 54 stored in the specimen storage section 52 and the reagent 58 stored in the reagent storage sections 56, immediately after the specimen 54 and the reagents 58 meet with each other in the reaction flow path 60 being a reaction section, and immediately thereafter, the cooling device 136B can perform cooling, which allows execution of a test with high accuracy and excellence in reliability.

Further, since the heating device 136A and cooling device 136B being a separate heating device and cooling device are used, it is possible to stop cooling after performing heating by the heating device 136A and to perform cooling by the cooling device 136B, thus allowing quick cooling of the residual heat of the heating device 136A by the cooling device.

Such a heating device 136A is not particularly limited and can be a Peltier element, nichrome wire heater, sheathed heater, ITO film, warm air heater, heater with a thin metallic film (chrome, gold, pratinum, etc.) formed on a substrate.

Further, the cooling device 136B is not particularly limited and can be one with a Peltier element or water jacket, or the like.

Still further, the cooling device 136B can be a type which removes heat by compressing and expanding refrigerant, such as chlorofluorocarbon or hydrochlorofluorocarbon, with a compressor or the like.

Yet further, the cooling device can be a type that is directly pressed against the cooled section of the testing microchip 50 or by a method that feeds a cooled refrigerant in a pipe to the vicinity of the cooled section of the chip or removes heat by bridging a member (steel, copper, aluminum, single crystal silicon, etc.) with an excellent thermal conductivity between the cooling device and the cooled section of the chip.

Although, in the present embodiment, a cooling device 134 that contacts with the testing microchip 50 to control the temperature of the reagents or the like is arranged, the cooling device 134 is not particularly limited thereto, and a cooling device similar to the cooling device 136B, as described above, can also be adopted.

Further, although, in the present embodiment, the cooling device 134 that contacts with the testing microchip 50 and controls the temperature of the reagents or the like and particularly controls the temperature of the reaction flow paths 60, and the heating-cooling device 136 are provided on side of the system main body 10, the cooling device 134 and the heating-cooling device 136 can be, for example, Peltier devices to be provided on the side of the testing microchip 50 with a power source of current provided on the side of the system main body 10.

It is also possible to cool the mixed solution of the specimen 54 and reagent 58 until just before performing reaction processing by heating the solution as described above. For example, in the case of ICAN method, it is preferable to perform cooling to a range from 0 to 4° C.

Since it is possible to prevent denaturation of the mixed solution of the specimen and reagent, reagent and specimen, if necessary, by heat in the process before performing reaction processing, it is possible to execute a test with high accuracy and excellence in reliability.

In such a manner, by pushing out specimen solution and reagent solution from the respective storage sections to make them meet with each other, reactions necessary for analysis, such as gene amplification reaction, trapping of analyte or antigen and antibody reaction are started. Herein, once the analysis starts, liquid feed of the specimen and reagents, gene amplification based on mixing, reaction such as binding between analyte and probe, detection of reaction product and optical measurement are automatically executed as a serial continuous process; measured data is stored in a file as well as necessary conditions and recording matters; and measurement of biological material is automatically executed.

A unit in charge of control system related to various control of liquid feed, temperature and reaction, optical detection, collection and processing of data constructs the system main body together with micro pumps and the optical device.

The system main body is used commonly to various specimen samples when a testing microchip 50 is mounted thereon.

Regarding reaction of gene amplification and detection thereof, liquid feed order, capacity, timing, etc., as conditions having been set in advance and as a program, are incorporated in software loaded on the system main body as well as control of micro pumps and temperature and data processing of optical detection.

The detection device 144 that detects reaction in the micro flow path o0f the testing microchip 50 irradiates measuring light from, for example a LED or the like, onto a detection section on an analysis flow path for each test item, and detects transparent light or reflection light with an optical detection unit, such as a photomultiplier tube.

Since the micro integrated analysis system 1 in accordance with the invention has each component downsized and is convenient for carrying, the system is not limited in place and time for use and is excellent in workability and operability.

Further, since it is possible to perform quick measurement regardless of place and time, it is also usable for emergent medical care and personal use for home healthcare.

Still further as the micro pump unit 26 to be used for liquid feed is incorporated in the system main body, the testing microchip 50 can be used as a disposal type.

The system in accordance with the invention can be suitably used particularly for test of gene or nucleic acid.

In this case, the micro flow path of the testing microchip 60 is structured to be suitable for PCR amplification, and even for biological materials other than for gene testing, the basic flow path structure can be designed to be approximately the same.

Typically, it is only necessary to change the specimen pre-processing section, reagents and probes, wherein the disposition and number of liquid feed elements can be properly modified to be used.

Further, those skilled in the art can easily change the type of analysis, for example, by making adjustment including mounting reagents necessary for an immunoassay method on the testing microchip 50, changing flow path elements a little, and modifying the specifications.

Such biological materials other than gene include various kinds of metabolism materials, hormones, and proteins (including enzymes and antigens).

In a preferable embodiment of a testing microchip 50, a single chip includes: a specimen storage section charged with a specimen or a biological material (e.g. DNA) extracted from the specimen; a specimen pre-processing section to perform preprocessing of the specimen; a reagent storage section for storing the reagent used for probe binding reaction and detection reaction (including gene amplification reaction or antigen-antibody reaction); a positive control storage section for storing positive control; a negative control storage section for storing negative control; a probe storage section for storing a probe (e.g. a probe to be hybridized with the gene to be detected, the gene being amplified by gene amplification reaction); a micro flow path communicating with the respective storage sections; and a pump connecting section for connection with separate micro-pumps for feeding a liquid in the storage sections and flow paths.

This testing microchip 50 is connected with micro pumps through the pump connecting section 64 and feed the specimen 54 stored in the specimen storage section 52 or a biological material (for example, DNA or other biological materials) extracted form the specimen, and reagents 58 stored in the reagent storage sections, to the reaction flow paths 60.

Then, the specimen or the biological material and the reagents are mixed with each other and reactions are caused between them in a reaction section of the micro flow paths, for example, a section for gene amplification (in the case of protein, antigen-antibody reaction, etc.), and thereafter, processed solutions 62 having been produced by processing the reaction solutions and probes stored in the probe storage sections are fed to the detection section on the downstream side flow paths. In this way, the processed solutions 62 are mixed and bound (or hybridized) with the probes in the flow paths, and the biological materials are detected, based on the reaction products.

Further, the above described reaction and detection are performed likewise also for positive control stored in the positive control storage section and negative control stored in the negative control storage section.

Further, the specimen storage section 52 of the testing microchip 50 communicates with a specimen injection section, and temporarily stores the specimen and supplies the specimen to a mixing section.

Herein, the specimen injection section to inject the specimen from the top surface of the specimen storage section 52 is preferably formed with a stopple of an elastic body such as rubber material, or covered with a resin such as polydimethylsiloxane (PDM) or a reinforced film, so as to prevent infection and contamination and secure sealability.

For example, specimen in a syringe is injected via a needle penetrating thorough a stopple of a rubber material or a needle through a thin hole with a lid.

Herein, in the case of the needle penetrating through a stopple of a rubber material, the needle hole preferably closes up immediately after the needle is removed. A different type of specimen injection mechanism may be arranged.

Prior to mixing with the reagent 58, the specimen 54 injected into the specimen storage section 52 is pre-processed in the specimen pre-processing section provided on the flow path 60, by mixing the specimen 54 and processing solution 62, for example. Preferable specimen pre-processing is, for example, separation or condensation of analysis object (analyte) and deproteination.

Therefore, the specimen pre-processing section may include a separation filter, adsorption resin, beads, and the like.

A predetermined amount of necessary reagents are sealed in advance in the reagent storage section 56 of the testing microchip 50. Accordingly, it is not necessary to charge a necessary amount of reagent 58, each time of use, and the testing microchip 50 is ready to be used immediately.

Further, in the case of analysis of biological material in a specimen, reagents necessary for measurement are usually respectively known. For example, in the case of analysis of an antigen present in a specimen, an antibody against the antigen, preferably, reagent containing a monochronal antibody is used. The antibody is preferably labeled with biotin and FITC.

Reagents for gene testing may contain, if necessary, pre-processing reagents to be used in specimen pre-processing, described above, as well as various reagents used for gene amplification, probes used for detection and chromogenic reagents.

The driving liquid 29 is supplied from micro pumps to push out specimen solution and reagent solution from the respective storage sections to make them meet with each other, and thus reactions necessary for analysis, such as gene amplification reaction, trap of analyte and antigen-antibody reaction are started.

The mixing of reagent and reagent, and the mixing of specimen and reagent can be done in a single mixing section at a desired mixing rate. Or, the mixture can be done by dividing either one or both of them, and a plurality of mixing sections are provided to mix at a desired mixing rate ultimately.

In this case, the embodiment of a reaction part is not particularly limited, and various embodiments and forms are allowed.

As an example, a micro flow path in which solutions are diffused and mixed is provided after a confluent section (flow path branch point) in which two or more liquids including reagent meet with each other, and reaction is performed in a liquid reservoir formed with a space with a greater width than that of the micro flow path and provided after the downstream side end portion of the micro flow path.

Herein, as a DNA amplification method, PCR amplification methods, which are widely applied in various fields, can be used. Various conditions to execute the amplification technology are studied in details and are described in various documents and improvements as well.

ICAN (Isothermal chimera primer initiated nucleic acid amplification) method having been developed recently has a feature to execute DNA amplification in a short time under an arbitrary certain temperature in a range from 50 to 60° C. (U.S. Pat. No. 3,433,929).

Accordingly, ICAN method is an amplification technology suitable for easy temperature control in using the testing microchip 50 in accordance with the invention.

With ICAN method, it takes about one hour by manual operation, however, a testing microchip in accordance with the invention takes 10 to 20 minutes, and preferably 15 minutes to complete a test including analysis.

On the downstream side from the reaction part in the micro flow path of the testing microchip 50, there is provided a detection part to detect analyte, such as an amplified gene.

The detection portion thereof, at least, is made of transparent material, preferably a transparent plastic, to enable optical measurement.

Further, biotin affinic protein (avidin, streptoavidin, extraavidin (R), preferably streptoavidin) adsorbed on the detecting section in the minute flow path is bound specifically with biotin labeled with a probe material or biotin labeled at 5' end of a primer used for gene amplification reaction.

Thereby, the probe labeled with biotin or the amplified gene is trapped by the present detecting part.

The detecting method of separated alnalyte or a DNA of an amplified target gene is not limited, however, as a preferred embodiment, basically it is conducted in the following procedure.

(1a) A specimen or DNA extracted from a specimen, or a cDNA synthesized by reverse transcript reaction from a specimen or from a RNA extracted from a specimen, and a primer which is modified by biotin at 5' position, are fed from their storage sections to the micro flow path in the downstream.

After conducting a process of gene amplification in the micro flow path of the reacting part, a process in which the amplified gene is denatured into a single-strand, by mixing amplified reaction solution containing the gene amplified in the micro flow path with denaturation solution. Then, the single-strand is hybridized with a probe DNA of which end is fluorescently labeled with FITC (fluorescein isothiocyanate).

Next, the hybrid is fed to a detection part in the micro flow path having adsorbed biotin affinity protein, and the amplified gene is trapped by the detection part in the micro flow path. Instead, the amplified gene may be hybridized with a fluorescently labeled probe DNA after being trapping by the detection part.

(1b) A specific antibody against analyte, such as an antigen, metabolism material or hormone present in the specimen, preferably reagent containing a monochronal antibody, is mixed with the specimen. Herein, the antibody is labeled with FITC.

Accordingly, the product obtained from antigen-antibody reaction contains biotin and FITC.

This is fed to the detection part in the micro flow path with the biotin-affinic protein (preferably streptavidin) adsorbed therein, and is fixed to the detection part through binding between the biotin-affinic protein and biotin.

(2) The gold colloid solution whose surface is modified with the anti-FITS antibody that specifically binds to the FITC is fed into the micro flow path. The gold colloid is adsorbed by the FITC of the fixed analyte/antibody reaction product, or by the FITC modified probe hybridized with the gene.

(3) The concentration of the gold colloid in the aforementioned micro flow path is optically measured.

The present invention provides a micro integrated analysis system using a chip that includes a micro flow path for which rigorous temperature distribution control is performed.

With a micro integrated analysis system in accordance with the invention, it is possible to heat or cool only a predetermined area of a chip micro flow path selectively and uniformly, and satisfactorily prevent heating and cooling of neighboring flow paths. Further, by inhibiting transfer of residual heat of the heating part to the neighboring flow paths and narrowing the intermediate temperature area at the both end portions of the micro flow path selectively heated, as much as possible, it is possible to make the temperature distribution in the chip as rigorous as possible. Further, it is possible to prevent creation of side reaction and loss of reagents from flow paths due to the presence of such an intermediate temperature area.

According to the invention, the heating-cooling device can heat mixed solution of the specimen and reagent immediately after the specimen stored in the specimen storage section and the reagent stored in the reagent storage section are mixed with each other and perform reaction processing, and perform cooling immediately thereafter, in the reaction section.

Accordingly, it is possible to quickly heat the mixture up to a necessary temperature when the mixed reagent having been mixed in the confluent section and the specimen from the specimen storage section have met with each other and got mixed with each other in the mixing and reaction flow path.

Still further, when the temperature has became a necessary temperature, it is possible to perform heating for a time period necessary for reaction and perform quick cooling so as to prevent creation of gas bubbles and side reaction, thereby allowing an accurate test excellent in reliability.

A preferred embodiment in accordance with the invention has been described above, however, the invention is not limited thereto. For example, although, in the above embodiment, ICAN method is used for the testing microchip for gene testing, various modifications may be made to disposition, shape, dimensions, size and the like, in accordance with the kind of specimen and the testing items.

Further, in the above embodiment, the testing microchip 50 is loaded on the chip conveying tray 22 and taken into the system main body 10 through the testing chip gateway 14 to be mounted. However, it is also possible to adopt a mechanism with which the chip conveying tray is not provided and the testing microchip 50 is directly inserted into the main body like in the case of a card reader, or a method can be applied in which an opening and closing door is provided and the testing microchip 50 is mounted at a testing position. In addition to these examples, various modifications can be made within the scope not departing from objects of the present invention.

What is claimed is:

1. A micro integrated analysis system, comprising:
   a plurality of micro pumps for injecting a specimen and reagent;
   a testing chip that includes:
      a pump connecting section having flow path openings to communicate with respective micro pumps of the plurality of micro pumps;
      a mixing flow path for mixing a specimen and reagent injected by the respective micro pumps and for reaction processing by heating; and
      a testing flow path for performing a predetermined test of a mixed solution having been mixed and processed for reaction in the mixing flow path;
   a system main body that includes:
      a holding section to hold the testing chip;
      the micro pumps;
      a heating section for heating the mixing flow path of the held testing chip, wherein the heating section is configured to selectively heat a portion of the mixing flow path; and
      a detection section for performing a test of the mixed solution in the testing flow path of the testing chip; and
   a heat insulating section provided in at least one of the testing chip and the system main body, the heat insulating section being arranged on both an inlet end and outlet end of the portion of the mixing flow path, wherein the heat insulating section is heat insulation oil charged in the both ends of the portion of the mixing flow path.

2. The micro integrated analysis system of claim 1, wherein the heat insulating section is a part of the testing chip that is in a vicinity of the both ends of the heated flow path and made of a material with a thermal conductivity not greater than 10 W/m·K.

3. The micro integrated analysis system of claim 1, wherein the testing chip is formed with a serial micro flow path in which, after the testing chip is mounted on the system main body in a state where the pump connecting section of the testing chip and a chip connecting section of a micro pump unit including the micro pumps are in tight liquid contact with each other, a specimen stored in a specimen storage section or a target material contained in a processed solution having been produced by processing the specimen in a flow path and reagent stored in a reagent storage section are fed to the mixing flow path to cause them to meet and react with each other, and thereafter a material produced by the reaction or a further processed material thereof is fed to the testing flow path so as to detect the produced material or the further processed material by the detection section.

4. The micro integrated analysis system of claim 3, wherein the reaction is a gene amplification reaction.

5. The micro integrated analysis system of claim 1, wherein the heated flow path is a flow path that constructs a reaction part for reaction between a target material and reagent.

6. The micro integrated analysis system of claim 1, wherein the micro pumps comprises:
   a first flow path of which flow path resistance varies with a differential pressure;
   a second flow path of which variation rate of a flow path resistance to variation in a differential pressure is smaller than that of the first flow path;
   a pressing chamber that is connected with the first flow path and the second flow path;
   an actuator that changes an inner pressure of the pressing chamber; and
   a driving device that drives the actuator.

7. The micro integrated analysis system of claim 1, wherein the heating section heats the heated flow path to perform reaction processing of the mixed solution immediately after the specimen and reagent are mixed in the mixing flow path, and the heat insulating section cools the flow paths continuing from the both ends of the heated flow path immediately after the reaction processing.

8. The micro integrated analysis system of claim 1, wherein the heat insulating section is controlled to cool the flow paths continuing from the both ends of the heated flow path during a time after the heating section heats the mixed solution of the specimen and reagent to perform reaction processing and before side reaction occurs.

9. The micro integrated analysis system of claim 1, wherein the heating section and heat-insulating section are constructed with a same Peltier element that performs heating and cooling by switching an electric current.

10. The micro integrated analysis system of claim 1, wherein the heating section and heat-insulating section are provided as one heating and heat-insulating unit.

11. The micro integrated analysis system of claim 1, wherein the mixed solution of the specimen and reagent is cooled until just before the mixed solution is heated and processed for reaction.

12. A micro integrated analysis system, comprising:
   a plurality of micro pumps for injecting a specimen and reagent;
   a testing chip that includes:
      a pump connecting section having flow path openings to communicate with respective micro pumps of the plurality of micro pumps;
      a mixing flow path for mixing a specimen and reagent injected by the respective micro pumps and for reaction processing by heating; and
      a testing flow path for performing a predetermined test of a mixed solution having been mixed and processed for reaction in the mixing flow path;
   a system main body that includes:
      a holding section to hold the testing chip;
      the micro pumps;
      a heating section for heating the mixing flow path of the held testing chip, wherein the heating section is configured to selectively heat a portion of the mixing flow path; and
      a detection section for performing a test of the mixed solution in the testing flow path of the testing chip; and
   a heat insulating section provided in at least one of the testing chip and the system main body, the heat insulating section being arranged on both an inlet end and outlet end of the portion of the mixing flow path, wherein the heat insulating section is narrow flow paths that are arranged continuing from the both ends of the portion of the mixing flow path, the cross-sectional areas of the narrow flow paths being smaller than flow path cross-sectional areas at the both ends of the portion of the mixing flow path.

13. The micro integrated analysis system of claim 12, wherein the heat insulating section is a part of the testing chip that is in a vicinity of the both ends of the testing chip and made of a material with a thermal conductivity not greater than 10 W/m·K.

14. The micro integrated analysis system of claim 12, wherein the testing chip is formed with a serial micro flow path in which, after the testing chip is mounted on the system main body in a state where the pump connecting section of the testing chip and a chip connecting section of a micro pump unit including the micro pumps are in tight liquid contact with each other, a specimen stored in a specimen storage section or a target material contained in a processed solution having been produced by processing the specimen in a flow path and reagent stored in a reagent storage section are fed to the mixing flow path to cause them to meet and react with each other, and thereafter a material produced by the reaction or a further processed material thereof is fed to the testing flow path so as to detect the produced material or the further processed material by the detection section.

* * * * *